US012640239B2

(12) United States Patent
Edwards et al.

(10) Patent No.: US 12,640,239 B2
(45) Date of Patent: May 26, 2026

(54) FUNCTIONAL BIOMARKERS FOR STATIN THERAPY IN AGE-RELATED MACULAR DEGENERATION (AMD)

(71) Applicants: APELIOTUS TECHNOLOGIES, INC., Philadelphia, PA (US); MASSACHUSETTS EYE AND EAR INFIRMARY, Boston, MA (US)

(72) Inventors: John G. Edwards, Philadelphia, PA (US); Joan W. Miller, Winchester, MA (US); Demetrios Vavvas, Boston, MA (US)

(73) Assignees: APELIOTUS TECHNOLOGIES, INC., Philadelphia, PA (US); MASSACHUSETTS EYE AND EAR INFIRMARY, Boston, MA (US)

( * ) Notice: Subject to any disclaimer, the term of this patent is extended or adjusted under 35 U.S.C. 154(b) by 0 days.

(21) Appl. No.: 16/756,588

(22) PCT Filed: Oct. 17, 2018

(86) PCT No.: PCT/US2018/056372
§ 371 (c)(1),
(2) Date: Apr. 16, 2020

(87) PCT Pub. No.: WO2019/079515
PCT Pub. Date: Apr. 25, 2019

(65) Prior Publication Data

US 2020/0243170 A1 Jul. 30, 2020

Related U.S. Application Data

(60) Provisional application No. 62/573,293, filed on Oct. 17, 2017.

(51) Int. Cl.
*G16H 10/20* (2018.01)
*A61B 3/06* (2006.01)
(Continued)

(52) U.S. Cl.
CPC ............ *G16H 10/20* (2018.01); *A61B 3/063* (2013.01); *A61B 3/102* (2013.01); *A61B 5/4848* (2013.01); *A61K 31/40* (2013.01)

(58) Field of Classification Search
USPC ........................................................ 705/2-3
See application file for complete search history.

(56) References Cited

U.S. PATENT DOCUMENTS 7,901,682 B2 * 3/2011 Sabbadini .......... G01N 33/6893 435/7.1
11,331,295 B2 5/2022 Vavvas et al.
(Continued)

FOREIGN PATENT DOCUMENTS

WO 2005/023094 A2 3/2005
WO 2008/100613 A2 8/2008
(Continued)

OTHER PUBLICATIONS

Farnoodian, M. (2016). Endogenous inhibitors of angiogenesis, TSP1 and PEDF, as potential targets for treatment of exudative AMD (Order No. 10158076). Available from ProQuest Dissertations and Theses Professional. (1823572122) (Year: 2016).*
(Continued)

*Primary Examiner* — Bennett Stephen Erickson
(74) *Attorney, Agent, or Firm* — Robert C. Netter, Jr.; Dann, Dorfman, Herrell & Skillman

(57) ABSTRACT

Methods of using visual functions such as dark adaptation, low luminance visual acuity, low luminance deficit, contrast sensitivity and scotopic sensitivity as functional biomarkers for statin therapy in AMD. These biomarkers can be used, for example, to support clinical trials of statin therapy for AMD by identifying participants more likely to respond, by providing an early indication of response, or by serving as an endpoint; or to support treatment of AMD patients with statins by identifying patients more likely to respond, by
(Continued)

providing an early indication of responders vs. non-responders, or by confirming a treatment benefit.

36 Claims, 20 Drawing Sheets

(51) Int. Cl.

| | |
|---|---|
| ***A61B 3/10*** | (2006.01) |
| ***A61B 5/00*** | (2006.01) |
| ***A61K 31/40*** | (2006.01) |

(56) References Cited

U.S. PATENT DOCUMENTS

| | | | | |
|---|---|---|---|---|
| 2003/0065020 | A1 | 4/2003 | Gale et al. | |
| 2005/0250745 | A1 | 11/2005 | Seddon | |
| 2006/0275294 | A1* | 12/2006 | Omoigui | A61K 36/899 514/423 |
| 2010/0168606 | A1* | 7/2010 | Edwards | A61B 3/063 600/558 |
| 2012/0134929 | A1* | 5/2012 | McGrath | A61K 33/00 514/390 |
| 2012/0156202 | A1 | 6/2012 | Shantha | |
| 2013/0331393 | A1* | 12/2013 | Lewis | A61K 9/08 514/248 |
| 2014/0303013 | A1 | 10/2014 | Hageman | |
| 2015/0305615 | A1 | 10/2015 | Jackson et al. | |
| 2017/0325676 | A1* | 11/2017 | Lichtenauer | A61B 3/024 |
| 2018/0166174 | A1* | 6/2018 | Lewis | G16H 50/70 |

FOREIGN PATENT DOCUMENTS

| | | | |
|---|---|---|---|
| WO | 2013/093762 | A1 | 6/2013 |
| WO | 2015/023902 | A2 | 2/2015 |
| WO | 2015/052104 | A1 | 4/2015 |
| WO | 2017/066529 | A1 | 4/2017 |
| WO | 20150305615 | | 4/2017 |

OTHER PUBLICATIONS

Flores R, Carneiro Â, Tenreiro S, Seabra MC. Retinal Progression Biomarkers of Early and Intermediate Age-Related Macular Degeneration. Life (Basel). Dec. 27, 2021;12(1):36. doi: 10.3390/life12010036. PMID: 35054429; PMCID: PMC8779095. (Year: 2021 ).*

Ferris, et al., "New Visual Acuity Charts for Clinical Research" Am. J. Opthalmology (1982) 94:91-96.

Ferris, et al., "Standardized Illumination for Visual Acuity Testing in Clinical Research" Am. J. Opthalmology (1982) 94:97-98.

Seddon, et al., "Progression of Age-Related Macular Degeneraation" Arch. Opthalmology (2005) 123:774-782.

Copenheaver, Blaine, "International Search Report and Written Opinion for PCT/US2018/056372", Jan. 3, 2029.

Owsley, et al., "Comparison of Visual Function in Older Eyes in the Earliest Stages of Age-Related Macular Degeneration to Those in Normal Macular Health," Current Eye Research, Mar. 24, 2015, vol. 41, No. 2, pp. 266-272.

Gehlbach, P., et al., "Statins for age-related macular degeneration (Review)" Cochrane Database of Systematic Reviews (2016) 8:CD006927, pp. 1-33.

Guymer, R.H., et al., "Proof of Concept, Randomized, Placebo-Controlled Study of the Effect of Simvastatin on the Course of Age-Related Macular Degeneration" PLoS ONE (2013) 8(12): e83759.

Jackson, et al., "Diagnostic sensitivity and specificity of dark adaptometry for detection of age-related macular degeneration" Invest Ophthalmol Vis Sci (2014) 55(3):1427-31.

Jackson, et al., "A short-duration dark adaptation protocol for assessment of age-related maculopathy" J Ocul Biol Dis Infor (2008) 1(1):7-11.

* cited by examiner

FUNCTIONAL BIOMARKERS FOR STATIN THERAPY IN AGE-RELATED MACULAR DEGENERATION (AMD)

CROSS-REFERENCE TO RELATED APPLICATIONS

This application is a national stage under 35 U.S.C. 371 of International Application No. PCT/US2018/056372, filed Oct. 17, 2018 (published). International Application No. PCT/US2018/056372 cites the priority of U.S. Provisional Application No. 62/573,293, filed Oct. 17, 2017 (expired).

TECHNICAL FIELD

Described herein are methods of using visual functions such as dark adaptation, low luminance visual acuity, low luminance deficit, contrast sensitivity, and scotopic sensitivity as functional biomarkers for statin therapy in AMD. These biomarkers can be used, for example, to support clinical trials of statin therapy for AMD by identifying participants more likely to respond, by providing an early indication of response, or by serving as an endpoint; or to support treatment of AMD patients with statins by identifying patients more likely to respond, by providing an early indication of responders vs. non-responders, or by confirming a treatment benefit.

BACKGROUND

Age-related macular degeneration (AMD) is a multifactorial heterogeneous disease, with at least 100 different at-risk genes reported in the literature and with several different phenotypes, including types and size of drusen (Miller, 2013 *Am J Ophthalmol* 155(1):1-35.e13). AMD is the leading cause of irreversible vision loss in adults in the Western world (Wong et al., 2014 *Lancet Glob Health* 2(2):e106-16).

AMD is broadly classified into two types. The atrophic or "dry" form is the most prevalent, characterized by accumulation of extracellular deposits, termed drusen, between the retinal pigmented epithelium (RPE) and the choroid. Progression to advanced AMD may involve, for example, atrophy of the RPE and/or one or more photoreceptors, and/or abnormal choroidal neovascularization (neovascular or "wet" AMD). Though it is less prevalent than the dry form, neovascular AMD is associated with rapid vision loss. However, despite effective antiangiogenic treatments for neovascular AMD, effective treatments are lacking for the more prevalent dry form.

One of the hallmark manifestations of AMD is the accumulation of drusen, the components of which are derived from local tissues (RPE/retina) and from the circulation (Curcio et al., 2011 *Br J Ophthalmol* 95(12):1638-45; Wu et al., 2010 *J Neurochem* 114(6):1734-44). Also associated with AMD are drusenoid pigment epithelial detachments (PEDs), in which the retinal pigment epithelium separates from the underlying Bruch's membrane due to the presence of one or more drusen. Drusen can be hard drusen or soft drusen. "Hard" drusen are small, distinct and far away from one another, and may not cause vision problems for a long time, if at all. "Soft" drusen have poorly defined edges, are large, and cluster closer together. Lipids are a major constituent of drusen, with esterified cholesterol (EC), unesterified cholesterol (UC), and phosphatidyl choline constituting 40% of the volume of hard drusen. Soft drusen are more fragile than hard drusen and oily upon dissection, consistent with high lipid constitution. The presence of soft drusen is one of the major risk factors for the subsequent development of advanced dry or wet AMD.

SUMMARY

To make clinical trials and other studies of statin therapy for AMD more practical and affordable and to reduce risk in treatment of AMD patients using statin therapy, there is a need for biomarkers that are more sensitive to AMD pathology, and in particular functional biomarkers linked to the mechanism of action for statin therapy. As disclosed herein, visual functions such as dark adaptation, low luminance visual acuity, low luminance deficit, contrast sensitivity, and scotopic sensitivity can be used as functional biomarkers in AMD. These biomarkers can be used, for example to support clinical trials of statin therapy for AMD by identifying participants more likely to respond, by providing an early indication of response, or by serving as an endpoint; or to support treatment of AMD patients with statins by identifying patients more likely to respond, by providing an early indication of responders vs. non-responders, or by confirming/demonstrating a treatment benefit.

Described herein are methods that include measuring one or more functional biomarkers in a subject who has age-related macular degeneration (AMD) to provide a baseline value (i.e., a value based on or derived from the one or more functional biomarker measurements); administering a treatment comprising a statin to the subject; measuring the one or more functional biomarkers to provide a corresponding subsequent value (i.e., a value determined in the same fashion as the baseline value from the one or more functional biomarker measurements) at a second or later time point; and optionally comparing the baseline value to the corresponding subsequent value.

Also described herein are methods for determining or predicting efficacy of a treatment for AMD in a subject, wherein the treatment comprises administration of a statin.

In certain embodiments, such treatment for AMD may have as the objective preventing or delaying progression of AMD in a subject (for example, to prevent or delay atrophy of the RPE, to prevent or delay atrophy of one or more photoreceptors, to prevent or delay vision loss, and/or to prevent or delay progression from early AMD to advanced AMD). In certain embodiments, such treatment for AMD may have as the objective regression of AMD in a subject (for example, regression of drusen, regression of PEDs, and/or improvement in visual acuity). The methods include identifying the subject as having AMD; measuring one or more functional biomarkers in the subject to provide a baseline value; administering a statin treatment to the subject; measuring the one or more functional biomarkers to provide a corresponding subsequent value at a second or later time point; and optionally comparing the baseline value to the corresponding subsequent value. In some embodiments, an improvement or no change from the baseline value indicates that the treatment is effective or likely to be effective for treatment of AMD in the subject. For example, when the goal of the treatment is stopping or slowing progression of AMD in the subject, no change from the baseline value indicates that the treatment is effective or likely to be effective. In some embodiments, a worsening or no change from the baseline value indicates that the treatment is ineffective or likely to be ineffective for treatment of AMD in the subject. For example, when the goal of the treatment is regression of AMD in the subject, no change from the baseline value indicates that the treatment is ineffective or likely to be ineffective.

In some embodiments, measuring one or more functional biomarkers comprises measuring one or more of dark adaptation, low luminance visual acuity, low luminance deficit, contrast sensitivity, or scotopic sensitivity.

In some embodiments, the second or later time point is one or more of about 1, 2, 3, 4, 5, 6, 8, 9, 10, 11, 12, 24, and/or 36 weeks; 30, 60, 90, 180, 270 and/or 365 days; or 1, 2, 3, and/or 4 quarters after initiation of the treatment. In some embodiments, the second or later time point is one or more of about 1, 2, 3, 4, 5, 6, 8, 9, 10, 11, 12, 24, and/or 36 weeks; 30, 60, 90, 180, 270 and/or 365 days; or 1, 2, 3, and/or 4 quarters after the baseline value is determined.

In some embodiments, the subject is a candidate being screened for a clinical trial, or a participant in a clinical trial. In some embodiments, the subject is not in a clinical trial. In some embodiments, the subject is a patient being managed by a physician outside of a clinical trial.

In some embodiments, the comparison of the baseline value to the corresponding subsequent value is used as a primary or registration endpoint to determine success or failure of a clinical trial, as a secondary endpoint in a clinical trial, or as an exploratory endpoint in a clinical trial, wherein the clinical trial involves the administration of a statin to subjects with AMD.

Also provided herein are methods for selecting a therapy for a subject who has AMD (or selecting a subject for a therapy). The methods include identifying a subject as having AMD; measuring one or more functional biomarkers in the subject to determine a subject value (i.e., a value based on or derived from the one or more functional biomarker measurements); and comparing the subject value to a corresponding reference range (i.e., a reference range for the subject value). The methods can also optionally include identifying the subject as having a subject value within the reference range and selecting a therapy comprising statin administration for the subject, or identifying the subject as having a subject value outside the reference range and selecting a therapy not comprising statin administration for the subject.

In some embodiments, the presence of a subject value within the reference range indicates that the subject is suitable for treatment with a statin therapy.

In some embodiments, the methods include administering a therapy comprising statin administration to the subject who has a subject value within the reference range.

Also provided herein are methods for selecting or identifying subjects for participation in or exclusion from a clinical trial of a statin therapy for AMD. The methods include optionally identifying the subject as having AMD; measuring one or more functional biomarkers in the subject to provide a subject value; comparing the subject value to a corresponding reference range; and identifying the subject as having a subject value within the corresponding reference range and being appropriate for inclusion in the trial, or identifying the subject as having a subject value outside the corresponding reference range and being appropriate for exclusion from the trial.

In some embodiments, the methods include including a subject in the clinical trial who is identified as being appropriate for inclusion. In some embodiments, the methods include excluding a subject from the clinical trial who is identified as being appropriate for exclusion.

Also provided herein are methods for stratifying subjects who have AMD and are participating in a clinical trial of a statin therapy for AMD. The methods include measuring one or more functional biomarkers in the subject to provide a subject value for each subject; and stratifying the subjects based on the subject values.

In some embodiments of the methods described herein, measuring one or more functional biomarkers comprises measuring one or more of dark adaptation, low luminance visual acuity, low luminance deficit, contrast sensitivity, or scotopic sensitivity.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. When a specific method is referenced for accomplishing a specific task or result, the specific method will not be replaceable by other methods known in the art unless stated otherwise herein. The materials, methods, and examples are illustrative only and not intended to be limiting. All publications, patent applications, patents, sequences, database entries, and other references mentioned herein are incorporated by reference in their entirety unless otherwise indicated. In case of conflict between information incorporated by reference and the present specification, the present specification, including definitions, will control.

Other features and advantages of the invention will be apparent from the following detailed description and figures, and from the claims.

DETAILED DESCRIPTION

As disclosed herein, visual functions such as dark adaptation, low luminance visual acuity, low luminance deficit, contrast sensitivity, and scotopic sensitivity can be used as functional biomarkers in subjects receiving statin administration for treatment of AMD. These functional biomarkers can be used to support clinical trials of statin therapy for AMD, for example by identifying participants who are more likely to respond, providing an early indication of response, or serving as an endpoint. They can also be used to support treatment of AMD patients using statin therapy, for example by identifying patients more likely to respond, providing an early indication of responders vs. non-responders, or confirming/demonstrating a treatment benefit.

In the present specification, the functional biomarkers described represent aspects of visual function and can be characterized by a variety of parameters as described herein. The various parameters that characterize the functional biomarkers are used herein to characterize a subject, evaluate a subject, or evaluate a response of a subject to statin treatment/therapy for AMD (the subject value, baseline value, and subsequent values described herein). As an example, the functional biomarker dark adaptation can be characterized by a parameter known as the rod intercept time. The rod intercept time is determined from measurements of dark adaptation and is referred to herein as a subject value, a baseline value, and a subsequent value in the methods described.

Figure 1:
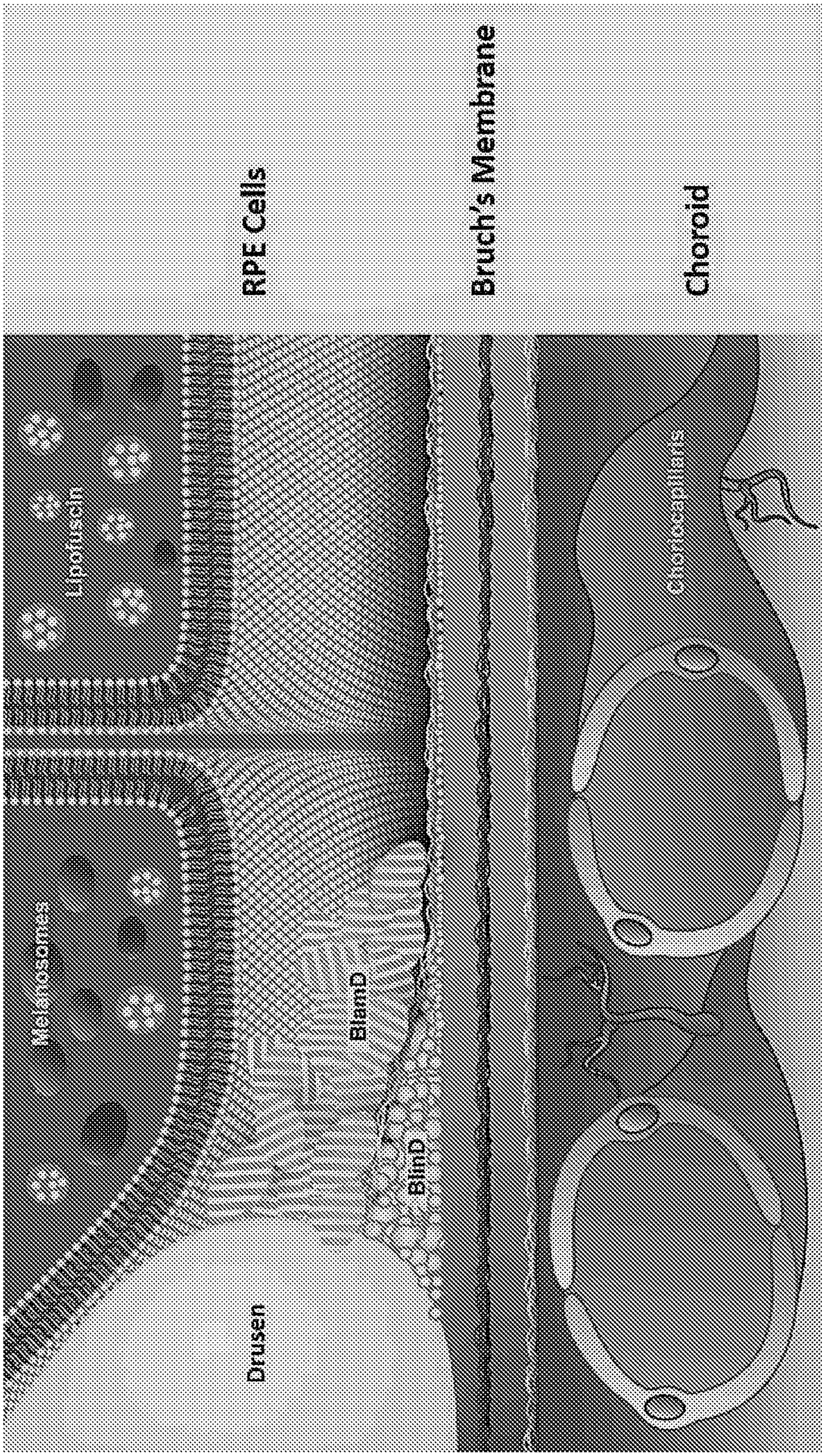
FIG. 1 illustrates the process of drusen formation (adapted from Miller, 2016 *Invest Ophthalmol Vis Sci.* 57:6911-6918).

The disclosed functional biomarkers are impacted by several aspects of AMD such as inflammation, oxidative stress, and impaired retinal cell metabolism. Of particular interest, the early stages of the AMD disease process are characterized by accumulation in the retina of extracellular deposits of cholesterol called drusen. Conventional drusen form between the basal lamina of the retinal pigmented epithelium (RPE) and Bruch's membrane (BM). As illustrated in FIG. 1, histopathologic studies have shown that these drusen start as a thin layer spanning the macula (known as basal linear deposits or BlinD) and progress to regions of thicker accumulation (known as basal laminar deposits or BlamD) (Curcio et al., 2011 *Br J Ophthalmol* 95:1638-1645; Miller, 2016 *Invest Ophthalmol Vis Sci* 57:6911-6918). The accumulation eventually mounds in some locations to the point where it can be detected clinically in fundus photographs as the tip of the underlying cholesterol iceberg. One consequence of the process of drusen accumulation is that the cholesterol layers coating BM act as a transport barrier between the RPE on one side of BM and the choroid on the other side. This transport barrier impedes the supply of oxygen and nutrients coming from the choroid to the RPE and the removal of waste products going the opposite direction. This in turn impacts the visual cycle, which in turn, impacts the disclosed functional biomarkers.

Figure 2:
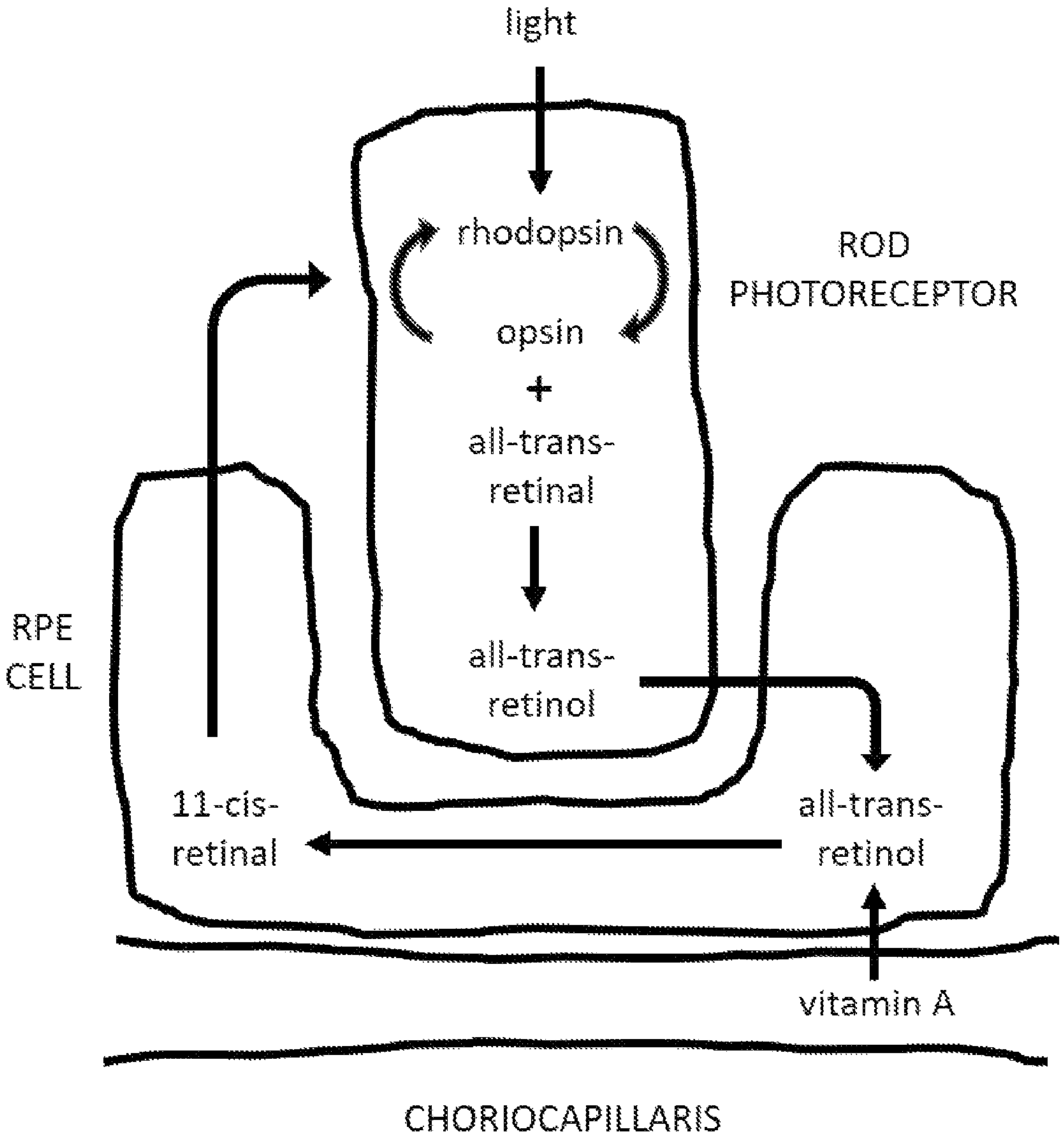
FIG. 2 illustrates the rhodopsin visual cycle.

The disclosed functional biomarkers are mediated at least in part by the visual cycle. The biochemistry of the visual cycle centers on successive photobleaching and regeneration of the photoreceptor visual pigments (opsins) (Saari, 2012 *Annu Rev Nutr* 32:125-45). There are three types of photoreceptors: rods, cones and retinal ganglion cells. FIG. 2 illustrates the biochemistry of the rod visual pigment (rhodopsin), although the biochemistry of the cone pigments (photopsin types I, II, and III) and the retinal ganglion pigment (melanopsin) is thought to be very similar. Rhodopsin consists of 11-cis-retinal and the protein opsin, and is tightly bound in the outer segment of the rods. 11-cis-retinal is the photoreactive portion of rhodopsin, which is converted to all-trans-retinal when a photon of light in the active absorption band strikes the molecule. This process goes through a sequence of chemical reactions as 11-cis-retinal isomerizes to all-trans-retinal. During this series of chemical steps, the nerve fiber, which is attached to the rod photoreceptor, undergoes a stimulus that is ultimately perceived in the brain as a visual signal. Following the breakdown of 11-cis-retinal to all-trans-retinal, the 11-cis-retinal is regenerated in the RPE cells by a series of steps that result in 11-cis-retinal being available for recombination with opsin protein. A sustaining supply of 11-cis-retinal is derived from vitamin A coming to the RPE cells from the choroid. The transport barrier described above (BlinD, BlamD, and/or drusen) slows the replenishment of vitamin A, interferes with the visual cycle, and in turn impacts the disclosed functional biomarkers. For example, there is a marked delay in dark adaptation even at the earliest stages of AMD, and the amount of delay increases with disease severity (Jackson et al, 2014 *Invest Ophthalmol Vis Sci* 55:1427-1431).

More recently it has been recognized that cholesterol can also accumulate on the epical side of the RPE between the RPE and the photoreceptor outer segments, forming what is known as subretinal drusenoid deposits (SDDs) or reticular pseudo drusen (Curcio et al., 2013 *Retina* 33(2):265-276). While the mechanism is not yet completely understood, SDDs have an even more profound effect than conventional drusen on the disclosed functional biomarkers, including for example dark adaptation (Flamendorf et al., 2015 *Ophthalmology* 122(10):2053-2062).

Provided herein are methods that can include the development or use of statin therapy for treatment of AMD in a subject. As used herein, a "subject" is a mammal, particularly a human, and includes subjects who are in a clinical trial or applying for a clinical trial, or whose care is being managed by a physician outside of a clinical trial. The terms "patient" and "subject" are used interchangeably herein. For example, the methods provided can be used to support the development or use of statin therapy intended to regress drusen (e.g., soft drusen), to regress PEDs, to prevent or delay atrophy of the RPE, to prevent or delay atrophy of one or more photoreceptors, to prevent or delay vision loss, to improve vision (e.g., visual acuity), and/or to prevent or delay progression from early AMD to advanced AMD (e.g., geographic atrophy or choroidal neovascularization). In some embodiments, the subjects have soft drusen, e.g., methods for development or use of statin therapy in AMD subjects identified as having soft drusen. In some embodiments, the subjects are determined after clinical assessment to have early AMD, e.g., methods for development or use of statin therapy in AMD subjects identified as having early AMD. In some embodiments, the subjects are determined after clinical assessment to have intermediate AMD, e.g., methods for development or use of statin therapy in AMD subjects identified as having intermediate AMD. In some embodiments, the subjects have SDDs, e.g., methods for development or use of statin therapy in AMD subjects identified as having SDDs. As used herein, the term "prevent" means to reduce the risk of, and need not be 100% prevention in all cases.

The methods can include determining a baseline value and comparing it to a corresponding subsequent value that is determined in the same fashion as the baseline value at a second or later time point. The baseline and subsequent values are based on or derived from measurement of one or more functional biomarkers in the subject as discussed herein. In some embodiments, the baseline and subsequent values can simply be the output associated with any one functional biomarker measurement (e.g., the dark adaptation rod intercept time or the number of Early Treatment Diabetic Retinopathy Study (ETDRS) letters of low luminance deficit). However, determination of baseline and subsequent values can also be based on or derived from a combination of multiple functional biomarker measurements, such as, for example, counting the number of measurements that indicate abnormal function (e.g., dark adaptation and low luminance deficit are measured and both measurements fall within their respective normal range, so the value assigned is "0", or only one falls within its normal range so the value assigned is "1", or neither falls within its normal range so the value assigned is "2"). Any manner of combination can be used.

The methods can include determining a subject value and comparing it to a corresponding reference range, wherein the presence of a subject value within the reference range indicates, for example, that the subject is suitable for treatment with a statin therapy, treatable with a statin therapy, likely to respond to a statin therapy, should continue to be treated with a statin therapy, or should be selected for inclusion in a clinical trial for a treatment with a statin therapy. The subject value is based on or derived from measurement of one or more functional biomarkers in the subject in the same manner as discussed above for baseline and subsequent values (i.e., the subject value can simply be the output associated with any one functional biomarker measurement, or it can be based on or derived from any manner of combination of multiple functional biomarker measurements). Suitable reference ranges can be determined using methods known in the art, e.g., using standard clinical trial methodology and statistical analysis. The reference range can have any relevant form. In some cases, the reference range comprises a predetermined range that represents a normal range for the subject value, e.g., a range for unaffected (healthy) subjects or subjects who are not at risk of developing AMD, or that represents an abnormal range for the subject value, e.g., associated with subjects who have AMD.

The reference range can be, for example, a range defined by cut-off (or threshold) values at both ends, such as the range inside or the range outside the cut-off values for a normal reference range, a confidence interval, a receiver operating curve, or a stratification by disease stage or other characteristics. The reference range can also be a range defined by a single cut-off (threshold) value at one end (e.g., the range below the cut-off value or the range above the cut-off value). The single cut-off value, or "cut-point", can be, for example, a median or mean, or a level that defines the boundary of an upper or lower quartile, tertile, or other segment of a clinical trial population or patient population that is determined to be statistically different from the other segments. The reference range can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk. In some embodiments, the predetermined level is a level or occurrence in the same subject, e.g., at a different time point, e.g., an earlier time point.

Dark Adaptation

Dark adaptation is preferably measured using devices known in the art, for example as described in U.S. Pat. No. 7,494,222. Dark adaptation is preferably measured using modifications of the methods known in the art, for example as described in U.S. Pat. No. 7,494,222. Briefly, the methods of the prior art as described therein, while sitting in complete or near-complete darkness the subject is first exposed to a bright photobleaching light to photobleach one or more of the visual pigments. This is followed by exposure to a series of dim stimulus lights to track visual sensitivity recovery from the photobleach. The intensity of the stimulus lights is gradually extinguished (generally in a staircase fashion), and the subject indicates whether each stimulus light presentation is detectable (e.g., by pushing a response button) or not detectable (e.g., by failing to push the response button). The just-detectible stimulus light intensity and the time at which it is detected are periodically recorded to generate a dark adaptation threshold curve. Finally, the speed of dark adaption is characterized by a parameter extracted from the threshold curve such as the rod intercept time or the rod-cone break time.

When referring to a dark adaptation parameter, for example, the rod intercept time, the dark adaptation parameter may be said to "improve," show "improvement," or "worsen," or show "worsening." The term "improve, or show "improvement" (as well as similar terms) means the dark adaptation parameter has changed in a beneficial manner as would be understood by the person of ordinary skill in the art. The term "worsen," show "worsening" (as well as similar terms) means the dark adaptation parameter has changed in a detrimental manner as would be understood by the person of ordinary skill in the art. For example, the dark adaptation parameter rod intercept time is improved when the rod intercept time decreases (for example 15 minutes to 10 minutes), while the dark adaptation parameter rod intercept time is worsened when the rod intercept time increases (for example from 10 minutes to 15 minutes).

In the case of dark adaptation, important parameters are bleach intensity and test location. The bleach intensity should be strong enough to ensure the subject is photobleached sufficiently to allow an accurate measurement of recovery, but not so strongly that the recovery time is impractically long. Bleach intensities from 10% effective bleach to 90% effective bleach are preferred. Bleach intensities from 50% effective bleach to 80% effective bleach are particularly preferred. Specific preferred embodiments are a 65% effective bleach, a 70% effective bleach and a 76% effective bleach. The test location should be selected to maximize sensitivity for the relevant AMD population. AMD is a slow deterioration of the macula, which occupies the central 20° of the retina. Functional impairment related to AMD progresses radially from near the center of the macula initially toward the periphery of the macula as the disease progresses. Test locations from 5° eccentricity (at the edge of the parafovea) to 20° eccentricity (at the edge of the macula) are preferred. Specific preferred embodiments are 5° eccentricity, 8.5° eccentricity and 12° eccentricity. Any azimuthal orientation can be used. A specific preferred embodiment is an azimuthal orientation on the inferior visual meridian. Determination of dark adaption can be based on any number of parameters including, but not limited to, rod intercept time (i.e., time for recovery to a criterion visual sensitivity level), rod-cone break time, rod recovery slope, and time to scotopic threshold. A specific preferred embodiment is the rod intercept time. When using the rod intercept time, criterion sensitivity levels from $5\times10^{-2}$ scotopic cd/m$^2$ to $5\times10^{-4}$ scotopic cd/m$^2$ are preferred. A specific preferred embodiment is $5\times10^{-3}$ scotopic cd/m$^2$.

In one embodiment, the following conditions are used for measuring the dark adaptation rod intercept parameter in any of the methods described herein: use of a 70% or 76% effective bleach, a 5° or 12° eccentricity test location, and a rod intercept criterion sensitivity level of $5\times10^{-3}$ scotopic cd/m$^2$.

In another embodiment, the following conditions are used for measuring the dark adaptation rod intercept parameter in any of the methods described herein: use of a 76% effective bleach, a 5° or 12° eccentricity test location, and a rod intercept criterion sensitivity level of $5\times10^{-3}$ scotopic cd/m$^2$.

In another embodiment, the following conditions are used for measuring the dark adaptation rod intercept parameter in any of the methods described herein: use of a 76% effective bleach, a 5° eccentricity test location centered on the inferior visual meridian, and a rod intercept criterion sensitivity level of $5\times10^{-3}$ scotopic cd/m$^2$.

In another embodiment, the following conditions are used for measuring the dark adaptation rod intercept parameter in any of the methods described herein: use of a 76% effective bleach, a 12° eccentricity test location centered on the inferior visual meridian, and a rod intercept criterion sensitivity level of $5\times10^{-3}$ scotopic cd/m$^2$.

Depending on the test parameters used and the subject's health status, dark adaptation times can vary from under 2 minutes to over 60 minutes. For example, using a 76% bleaching intensity, a 5° eccentricity test location, and a rod intercept criterion sensitivity level of $5\times10^{-3}$ scotopic cd/m$^2$, the rod intercept time for a normal, healthy subject will typically be under 6.5 minutes and the rod intercept time for an AMD patient will typically be over 6.5 minutes, with early AMD patients typically being around 13 minutes, intermediate AMD patients typically being around 17 minutes, and advanced AMD patients typically being 20 minutes or more. The rod intercept times above are generalizations and the rod intercept times for individual subjects may vary (for example, a subject with intermediate AMD may have a rod intercept time significantly less than 17 minutes). For dark adaptation, faster is better, and a decrease in dark adaptation time (e.g., a decrease in rod intercept time, rod-cone break time, rod recovery slope, or time to scotopic threshold) (e.g., by at least 1-3, 3-5 or 1-5 minutes) is an improvement in any of the methods described herein. In certain specific embodiments in any of the methods described herein, a decrease in rod intercept time of 1 minute, 1-3 minutes, 3-5 minutes, or 1-5 minutes) is an improvement.

AMD status has been determined in the art using a number of recognized grading systems, such as the Beckman AMD Classification System, the Age-Related Eye Disease Study (AREDS) Severity Scale, the AREDS Simplified Severity Scale, the International Classification and Grading System for AMD, and the Wisconsin Age-Related Maculopathy Grading System. When a determination of AMD status is required for a subject, the determination of AMD status is made using the Beckman AMD Classification System (Ferris et al. *Ophthalmology* 2013; 120:844-851).

Ad discussed herein, dark adaptation may be impacted by the accumulation of cholesterol and other lipids in the retina, even when such accumulation does not result in observable drusen formation. Statins are known to impact the levels of cholesterol and other lipids. As such, the use of dark adaptation as a functional biomarker brings to together a possible mechanism involved in AMD pathology and a possible mechanisms of action of the statins. Those in the art are aware that not all drugs that successfully treat AMD have an impact on visual functions like dark adaptation. For example, the administration of a compound that provides neuroprotection may improve AMD by strengthening the photoreceptors so they are less susceptible to AMD pathology; however, such compounds will not impact dark adaptation. Those in the art are aware that not all drugs that impact dark adaptation will successfully treat AMD. For example, administration of large doses of vitamin A will improve dark adaptation without improving AMD or lessening AMD pathology.

Low Luminance Visual Acuity/Low Luminance Deficit

Low luminance visual acuity and/or low luminance deficit are preferably measured using methods known in the art. One option is to use standard eye charts, for example as described in Sunness et al., 2008 *Ophthalmology* 115(9): 1480-1488. Briefly, a neutral density filter is placed between a normally illuminated eye chart and the subject's eye. As in measurement of normal luminance visual acuity, the subject is asked to start at the top line of the chart (with the largest letters) and read down as many lines or partial lines of letters as possible. Low luminance deficit is the difference between normal luminance visual acuity (measured with no intervening neutral density) and low luminance visual acuity (measured with an intervening neutral density). A variety of eye chart types can be used including Snellen charts and ETDRS charts. Important parameters are the eye chart luminance level and the amount of neutral density introduced for low luminance comparisons. Eye chart luminance levels from 70 $cd/m^2$ to 400 $cd/m^2$ are preferred. Specific preferred embodiments are 85 $cd/m^2$, 100 $cd/m^2$, and 130 $cd/m^2$. Neutral density filters from 1.0 log units (a factor of 10 reduction) to 3.0 log units (a factor of 1000 reduction) are preferred. A specific preferred embodiment is 2.0 log units.

Alternatively, electronic vision testers can be used to measure low luminance visual acuity and/or low luminance deficit, for example as described in Chandramohan et al., 2016 *Retina* 36(5):1021:1031. In this approach, normal and low luminance visual acuity are measured by displaying progressively smaller letters on an electronic screen having a high background luminance (e.g., 16 $cd/m^2$) or a low background luminance (e.g., 5 $cd/m^2$) for the respective measurements, and asking the subject to read as many letters as possible in each case. Low luminance deficit is again defined as the difference between normal luminance visual acuity and low luminance visual acuity.

The more letters that can be read, the better. For example, as with normal luminance visual acuity, low luminance visual acuity can range from less than 50 ETDRS letters (which is equivalent to 1.0 log MAR or 20/200 on the traditional US scale and considered "legally blind") to better than 100 ETDRS letters (which is equivalent to 0.0 log MAR or 20/20 on the traditional US scale and considered "normal"). AMD patients can fall anywhere along this range depending on disease severity. Intermediate AMD patients typically have a low luminance deficit of around 10 ETDRS letters and advanced AMD patients typically have a low luminance deficit of 20 ETDRS letters or more. A decrease in low luminance deficit (e.g., by at least 5-10, 10-15, or 5-15 ETDRS letters) is an improvement.

Contrast Sensitivity

Contrast sensitivity is the reciprocal of the smallest amount of contrast (i.e., degree of blackness to whiteness) that is required to be able to detect a target. Contrast sensitivity is preferably measured using standard methods, as described for example in Owsley, 2003 *Ophthalmol Clin N Am* 16:171-77. Tools for measuring contrast sensitivity include, for example, Pelli-Robson charts, Bailey-Lovie charts, Cambridge low contrast gratings, Regan charts, FACT charts, and computerized test systems such as the Spaeth/Richmond contrast sensitivity test. Briefly, letters or periodic patterns (such as sine wave or square wave gratings) having decreasing contrast are displayed on a chart or electronic screen, and the subject is asked to read or otherwise identify as many of these targets as possible. An important parameter is the background luminance level. Chart luminance levels from 10 $cd/m^2$ to 500 $cd/m^2$ are preferred. A specific preferred embodiment is 85 $cd/m^2$. The contrast of the targets can be characterized in a variety of ways. So-called Weber contrast (the luminance of the background minus the luminance of the target divided by the luminance of the background) is preferred for tools involving letters. So-called Michelson contrast (the luminance of the brightest area minus the luminance of the dimmest area divided by the sum of the two) is preferred for tools involving periodic patterns.

The more letters that can be read or targets that can be identified, the better. AMD patients typically have lower contrast sensitivity than normal subjects. For example, using a Pelli-Robson chart, contrast sensitivity for normal subjects typically ranges from 38 letters (equivalent to 1.9 log contrast sensitivity) to 31 letters (equivalent to 1.55 log contrast sensitivity), while contrast sensitivity for early, intermediate and late AMD patients is typically 27 letters (equivalent to 1.35 log contrast sensitivity), 24 letters (equivalent to 1.2 log contrast sensitivity), and 19 letters (equivalent to 0.95 log contrast sensitivity), respectively. An increase in letters read or targets identified (e.g., at least 3-5, 5-10 or 3-10 letters/targets) is an improvement.

Scotopic Sensitivity

Scotopic sensitivity is the dimmest light detectable in otherwise complete or near-complete darkness. Scotopic sensitivity is preferably measured using standard methods, as described for example in Wu et al., 2013 *Invest Ophthalmol Vis Sci* 54:7378-7385. Briefly, while sitting in complete or near-complete darkness the subject is exposed to a series of stimulus lights. The intensity of the stimulus lights is gradually extinguished (generally in a staircase fashion), and the subject indicates whether each stimulus light presentation is detectable (e.g., by pushing a response button) or not detectable (e.g., by failing to push the response button). The just-detectible stimulus light intensity is recorded as a scotopic sensitivity threshold. Scotopic sensitivity testing can be performed with or without prior dark adaptation. When testing is performed with prior dark adaptation, scotopic sensitivity can be characterized, for example, by a single threshold measurement or by averaging a few threshold measurements. When testing is performed without prior dark adaptation, scotopic sensitivity can be characterized, for example, by measuring thresholds until there is little or no change in the threshold value. Scotopic sensitivity measurements can be made, for example, using a microperimeter or a dark adaptometer.

In the case of scotopic sensitivity, important parameters are the background luminance level, the wavelength of the stimulus light, and the test location. Testing should be performed using a background luminance level as low as practically possible. A specific preferred background luminance level is 1.27 $cm/m^2$. The stimulus light wavelength is preferably matched to the spectral response curve of the rod photoreceptors that are primarily responsible for scotopic (or night) vision. Red light (i.e., wavelengths over 550 nm) is preferred. Specific preferred embodiments are wavelengths clustered around 627 nm and wavelengths clustered around 670 nm. Test locations within the macula are preferred (i.e., from 0° eccentricity to 20° eccentricity). Specific preferred test locations are 0° eccentricity, 1° eccentricity, 2.33° eccentricity, 4° eccentricity, 5° eccentricity, 6° eccentricity, 8.5° eccentricity, and 12° eccentricity. Any azimuthal orientation can be used. Analysis of scotopic sensitivity can be based on measurements at a single test location or a combination of measurements at multiple test locations, such as, for example, by calculating the average of scotopic sensitivity measurements for multiple test locations or by calculating the percentage of scotopic sensitivity measurements below a fixed criterion. The dimmer the light that can be seen in the dark, the better. Scotopic sensitivity is typically impaired in AMD patients vs. normal subjects. Quantification of scotopic sensitivity depends on the test parameters used and the subject's health status. For example, using a background luminance level of 1.27 $cm/m^2$, a stimulus light with wavelengths clustered around 627 nm (e.g., an LED having a central wavelength of 627 nm), and analyzing 37 central test locations ranging from 0° eccentricity to 5° eccentricity, the average scotopic sensitivity is typically reduced by 2 to 3 dB for patients having intermediate AMD vs. normal subjects (i.e., the dimmest light that can be seen in the dark by an intermediate AMD patient is typically 1.5 to 2 times brighter than the dimmest light that can be seen in the dark by a normal subject). Using the same test parameters, the percentage of locations with reduced scotopic sensitivity can be over 40% for intermediate AMD patients. A lessening of the reduction in average sensitivity or a lowering of the percentage of locations with reduced sensitivity would be an improvement.

Clinical Trial Support—Stratification/Endpoints

Administration of statins can be an effective therapy for AMD. For example, Vavvas et al. demonstrated that use of high-dose atorvastatin resulted in the disappearance of drusen deposits that are the structural hallmark of AMD and improvement in vision for 43% of patients treated (Vavvas et al., 2016 *EBioMedicine.* 5:198-203). However, additional clinical trials are needed to secure regulatory approvals from agencies such as the US Food and Drug Administration (FDA) and the European Medicines Agency (EMA). Because the clinical trial endpoints traditionally used to establish efficacy for ophthalmic indications—such as visual acuity and disease progression—are relatively insensitive biomarkers for AMD, clinical trials of AMD therapies generally require large numbers of study participants or long study durations, often making them cost prohibitive. To make clinical trials and other studies of statin therapy for AMD more practical and affordable, there is a need for biomarkers that are more sensitive to AMD pathology, and in particular for functional biomarkers linked to the mechanism of action for statin therapy. The disclosed functional biomarkers can be used, for example, as the basis for inclusion/exclusion criteria or clinical trial endpoints in the development of statins as a therapy for AMD.

In some methods, one or more of the functional biomarkers disclosed herein is measured at the initiation of a clinical trial to provide a subject value that indicates the likelihood of a treatment effect or a baseline value to track treatment effect. In some embodiments, an impaired subject value at the initiation of the clinical trial indicates the potential for treatment response; for example, allowing the trial investigators to decide whether the subject should be included in or excluded from the trial. During or after administration of a statin treatment under the clinical trial (e.g., at one or more of 1, 2, 3, 4, 5, 6, 8, 9, 10, 11, 12, 24, and/or 36 weeks, or 30, 60, 90, 180, 270 and/or 360 days, or 1, 2, 3, and/or 4 quarters after initiation of the treatment), the one or more functional biomarkers disclosed herein can be measured again to provide a subsequent value, and the subsequent value compared to the baseline value or an earlier subsequent value. In some embodiments, an improvement from the baseline value indicates that the therapy is effective or likely to be effective for the subject. In some embodiments, no change or a worsening from the baseline value indicates that the therapy is ineffective or likely to be ineffective. In some embodiments, for example in patients who are expected to experience rapidly worsening disease based on natural history, no change from the baseline value indicates that the therapy is effective or likely to be effective for the patient.

An advantage over endpoints traditionally used in ophthalmic clinical trials, such as visual acuity and disease progression, is greater sensitivity to AMD pathology. This is illustrated by a study using dark adaptation as an endpoint to evaluate the efficacy of vitamin A supplementation in AMD patients. In that study, Owsley et al. examined the effect of a short course of high-dose vitamin A (preformed retinol) in older adults with normal retinal health or AMD (Owsley et al., 2006 *Invest Ophthalmol Vis Sci* 47(4):1310-1318). A randomized, double-masked, placebo-controlled experiment was conducted. Adults at least 50 years old whose fundus photographs for the study eye fell within steps 1 through 9 (normal retinal health through intermediate AMD) of the extended AREDS Grading System were randomly assigned to a 30-day course of 50,000 international units of oral retinol or placebo. The study consisted of 104 patients with 52 each in the intervention and placebo groups. Dark adaptation (determined using the cone time constant, cone sensitivity, rod-cone break, rod slope, and rod sensitivity) and visual acuity were measured at baseline and 30-day follow-up. There was no difference between the groups for either parameter at baseline. At 30-day follow-up, the retinol intervention group had significantly faster dark adaptation than the placebo group. In addition, those patients having the greatest improvement in dark adaptation reported the greatest improvement in low luminance mobility using a standardized low luminance questionnaire. By contrast, there continued to be no difference in visual acuity between the groups. After an additional 30-day washout period, the improvement in dark adaptation reversed to the baseline level. This study also noted that the observed differences between treatment groups were similar in the subjects with AMD and without AMD. Similarly, it has been shown that low luminance deficit is a strong predictor of future visual acuity loss in AMD patients with geographic atrophy (Sunness et al., 2008 *Ophthalmology* 115(9):1480-1488) and is correlated with real-world vision-related difficulties experienced by patients with intermediate AMD (Wu et al., 2016) *Br J Ophthalmol* 100:395-398).

In some embodiments, the disclosed functional biomarkers can be used as the basis for a primary or registration endpoint to determine success or failure of the trial. In other embodiments, these biomarkers can be used as the basis for a secondary or exploratory endpoint to provide further elucidation of the trial results rather than a determination of ultimate success or failure. These biomarkers can also be used for patient selection and/or stratification; for example, the study population in the clinical trial can be selected and/or stratified/classified based on subject values derived from the biomarkers. Alternatively, these biomarkers can be used to provide an early indication of effectiveness at an interim look during a clinical trial that is ultimately based on a different primary endpoint not expected to show improvement as quickly; for example, allowing the trail sponsor to decide whether to terminate or continue the trial.

In some embodiments, when screening patients for inclusion in a clinical trial, those with an impaired functional biomarker (e.g., delayed dark adaptation or a larger than normal low luminance deficit) are more likely to respond to intervention, simply because they have deficits that can be corrected. In some embodiments, once treatment has started, improvement in a functional biomarker (e.g., a shortening of dark adaptation time or a lessening of low luminance deficit) is an early indicator of treatment efficacy and consequently indicates those more likely to have follow-on benefits such as disappearance of drusen or improvement in visual acuity.

Therefore, the following methods are provided in the present disclosure.

The present disclosure provides a method for selecting or identifying a subject for participation in or exclusion from a clinical trial of a statin therapy for treatment of AMD.

The method comprises the steps of: 1) optionally identifying the subject or having the subject identified as having AMD; 2) measuring or having measured one or more functional biomarkers in the subject; 3) determining or having determined a subject value for the subject from the one or more measurements of step 2; 4) comparing the subject value to a corresponding reference range; and 5) selecting or identifying the subject for participation if the subject value is within the corresponding reference range, or selecting or identifying the subject for exclusion if the subject value is outside the corresponding reference range. Such a method can further include enrolling a subject in the clinical trial who is identified as being appropriate for inclusion, excluding a subject from the clinical trial who is identified as being appropriate for exclusion, or a combination of the foregoing.

The present disclosure provides a method for selecting or identifying a subject for participation in or exclusion from a clinical trial of a statin therapy for treatment of AMD. The method comprises the steps of: 1) optionally identifying the subject or having the subject identified as having AMD; 2) measuring or having measured dark adaptation in the subject; 3) determining or having determined the rod intercept time from the dark adaptation measurement to provide a subject value; 4) comparing the subject value to a corresponding reference range; and 5) selecting or identifying the subject for participation if the subject value is within the corresponding reference range, or selecting or identifying the subject for exclusion if the subject value is outside the corresponding reference range. Such a method can further include enrolling a subject in the clinical trial who is identified as being appropriate for inclusion, excluding a subject from the clinical trial who is identified as being appropriate for exclusion, or a combination of the foregoing.

The present disclosure provides a method for stratifying a plurality of subjects who are participating in or may participate in a clinical trial of a statin therapy for treatment of AMD. The method comprises the steps of: 1) optionally identifying each of the plurality of subjects or having each of the plurality of subjects identified as having AMD; 2) measuring or having measured one or more functional biomarkers in each of the plurality of subjects; 3) determining or having determined a subject value for each of the plurality of subjects from the one or more measurements of step 2 to provide a subject value for each of the plurality subjects; and 4) stratifying the plurality of subjects based on the subject values.

The present disclosure provides a method for stratifying a plurality of subject who have AMD and are participating in or may participate in a clinical trial of a statin therapy for treatment of AMD. The method comprises the steps of: 1) optionally identifying each of the plurality of subjects or having each of the plurality of subjects identified as having AMD; 2) measuring or having measured dark adaptation in each of the plurality of subjects; 3) determining or having determined the rod intercept time for each of the plurality of subjects from the dark adaptation measurement to provide a subject value for each of the plurality of subjects; and 4) stratifying the plurality of subjects based on the subject values.

In any of the foregoing embodiments for stratifying a plurality of subject who have AMD and are participating in or may participate in a clinical trial of a statin therapy for treatment of AMD, the subject may be stratified based on AMD status (for example, early AMD, intermediate AMD, or late AMD) in addition to the above criteria. For example, a subject may be stratified in a clinical trial of a statin therapy for treatment of AMD due to the subject value (for example, rod intercept time) and type of AMD (for example, intermediate AMD).

The present disclosure provides a method for identifying an early indication of a response to a statin therapy in a clinical trial of the statin therapy for treatment of AMD. The method comprises the steps of: 1) optionally identifying the subject or having the subject identified as having AMD; 2) administering or having administered the statin therapy to the subject; 3) measuring or having measured one or more functional biomarkers in the subject; 4) determining or having determined a subject value for the subject from the one or more measurements of step 3; 5) comparing the subject value to a corresponding reference range; and 6) identifying an early indication of a response to the statin therapy in the subject if the subject value is within the corresponding reference range.

The present disclosure provides a method for identifying an early indication of a response to a statin therapy in a clinical trial of the statin therapy for treatment of AMD. The method comprises the steps of: 1) optionally identifying the subject or having the subject identified as having AMD; 2) administering or having administered the statin therapy to the subject; 3) measuring or having measured one or more functional biomarkers in the subject; 4) determining or having determined a baseline value for the subject from the one or more measurements of step 3; 5) measuring or having measured the one or more functional biomarkers in the subject at one or more second or later time points; 6) determining or having determined a corresponding subsequent value from the one or more measurements of step 5; and 7) identifying an early indication of a response to the statin therapy in the subject if a comparison of the subsequent value to the baseline value or an earlier subsequent value satisfies an early indication criteria.

The present disclosure provides a method for identifying an early indication of a response to a statin therapy in a clinical trial of the statin therapy for treatment of AMD. The method comprises the steps of: 1) optionally identifying the subject or having the subject identified as having AMD; 2) administering or having administered the statin therapy to the subject; 3) measuring or having measured dark adaptation in the subject; 4) determining or having determined the rod intercept time from the dark adaptation measurement to provide a subject value; 5) comparing the subject value to a corresponding reference range; and 6) identifying an early indication of a response to the statin therapy in the subject if the subject value is within the corresponding reference range.

The present disclosure provides a method for identifying an early indication of a response to a statin therapy in a clinical trial of the statin therapy for treatment of AMD. The method comprises the steps of: 1) optionally identifying the subject or having the subject identified as having AMD; 2) administering or having administered the statin therapy to the subject; 3) measuring or having measured dark adaptation in the subject; 4) determining or having determined the rod intercept time from the dark adaptation measurement to provide a baseline value; 5) measuring or having measured dark adaptation in the subject at one or more second or later time points; 6) determining or having determined the rod intercept time from the dark adaptation measurement to provide a subsequent value; and 7) identifying an early indication of a response to the statin therapy in the subject if a comparison of the subsequent value to the baseline value or an earlier subsequent value satisfies an early indication criteria.

In any of the foregoing methods for identifying an early indication of a response to a statin therapy in a clinical trial, such a method can further include continuing the subject in the clinical trial who has shown an early indication of a response to the statin therapy. In any of the foregoing methods for identifying an early indication of a response to the statin therapy in a clinical trial, such a method can be used to provide an early indication of efficacy at an interim period during the clinical trial, wherein the efficacy of the clinical trial is ultimately based on a different endpoint (such as the primary or registration endpoint) not expected to show improvement as quickly, to make a decision on continuing the clinical trial or terminating the clinical trial, or a combination of the foregoing.

In any of the foregoing methods for identifying an early indication of a response to a statin therapy in a clinical trial, the early indication criteria may be: i) no change in the subsequent value as compared to the baseline value or an earlier subsequent value; ii) an improvement in the subsequent value as compared to the baseline value or an earlier subsequent value; or iii) a worsening of less than 10% in the subsequent value as compared to the baseline value or an earlier subsequent value.

In any of the foregoing methods for identifying an early indication of a response to a statin therapy in a clinical trial, the early indication criteria may be: i) no change in the subsequent value (for example, rod intercept time) as compared to the baseline value or an earlier subsequent value; ii) an improvement in the subsequent value (for example, rod intercept time) as compared to the baseline value or an earlier subsequent value; or iii) a worsening of less than 180 seconds in the subsequent value (for example, rod intercept time) as compared to the baseline value or an earlier subsequent value.

In any of the foregoing embodiments for selecting or identifying a subject for participation in or exclusion from a clinical trial of a statin therapy for treatment of AMD, the subject may be identified or selected based on AMD status (for example, early AMD, intermediate AMD, or late AMD) in addition to the above criteria. For example, a subject may be identified as being appropriate for inclusion in a clinical trial of a statin therapy for treatment of AMD due to the subject value (for example, rod intercept time) falling within the corresponding reference range and due to having intermediate AMD.

The present disclosure provides a method for conducting a clinical trial of a statin therapy for treatment of AMD in a plurality of subjects. The method comprises the steps of: 1) optionally identifying the plurality of subjects or having the plurality of subjects identified as having AMD; 2) administering or having administered the statin therapy to the plurality of subjects; 3) measuring or having measured one or more functional biomarkers in the plurality of subjects; 4) determining or having determined a subject value for each of the plurality of subjects from the one or more measurements of step 3; 5) using the subject value as a clinical trial endpoint; and 6) optionally taking an action based on the clinical trial endpoint.

The present disclosure provides a method for conducting a clinical trial of a statin therapy for treatment of AMD in a plurality of subjects. The method comprises the steps of: 1) optionally identifying the plurality of subjects or having the plurality of subjects identified as having AMD; 2) administering or having administered the statin therapy to the plurality of subjects; 3) measuring or having measured one or more functional biomarkers in the plurality of subjects; 4) determining or having determined a baseline value for each of the plurality of subjects from the one or more measurements of step 3; 5) measuring or having measured the one or more functional biomarkers in each of the plurality of subjects at one or more second or later time points; 6) determining or having determined a corresponding subsequent value from the one or more measurements of step 5; 7) using as a clinical trial endpoint a comparison of the subsequent value to the baseline value (or an earlier subsequent value); and 8) optionally taking an action based on the clinical trial endpoint.

The present disclosure provides a method for conducting a clinical trial of a statin therapy for treatment of AMD in a plurality of subjects. The method comprises the steps of: 1) optionally identifying the plurality of subjects or having the plurality of subjects identified as having AMD; 2) administering or having administered the statin therapy to the plurality of subjects; 3) measuring or having measured dark adaptation in each of the plurality of subjects; 4) determining or having determined the rod intercept time from the dark adaptation measurement to provide a subject value; 5) using the subject value as a clinical trial endpoint; and 6) optionally taking an action based on the clinical trial endpoint.

The present disclosure provides a method for conducting a clinical trial of a statin therapy for treatment of AMD in a plurality of subjects. The method comprises the steps of: 1) optionally identifying the plurality of subjects or having the plurality of subjects identified as having AMD; 2) administering or having administered the statin therapy to the plurality of subjects; 3) measuring or having measured dark adaptation in each of the plurality of subjects; 4) determining or having determined the rod intercept time from the dark adaptation measurement to provide a baseline value; 5) measuring or having measured dark adaptation in each of the plurality of subjects at one or more second or later time points; 6) determining or having determined the rod intercept time from the dark adaptation measurement to provide a subsequent value; 7) using as a clinical trial endpoint a comparison of the subsequent value to the baseline value (or an earlier subsequent value); and 8) optionally taking an action based on the clinical trial endpoint.

In any of the foregoing embodiments for conducting a clinical trial, the endpoint may be a primary or registration endpoint to determine success or failure of the clinical trial. In any of the foregoing embodiments for conducting a clinical trial, the endpoint be a secondary or exploratory endpoint to provide an early indication of efficacy at an interim period during the clinical trial and/or to provide further elucidation of the trial results rather than a determination of ultimate success or failure.

In any of the foregoing methods for conducting a clinical trial, taking an action based on the clinical trial endpoint can be: i) determining or having determined an early indication of efficacy at an interim period during the clinical trial, wherein the efficacy of the clinical trial is ultimately based on a different endpoint (such as the primary or registration endpoint) not expected to show improvement as quickly; ii) making or having made a decision on continuing the clinical trial; iii) terminating or having terminated the clinical trial; iv) adding or having added additional subjects to the clinical trial; v) changing or having changed a parameter of the clinical trial (for example, adding or deleting a secondary endpoint; the dose of a statin, the type of statin administered, or the administration frequency of the statin); vi) or a combination of the foregoing.

In the foregoing methods for selecting or identifying a subject, methods for stratifying a plurality of subjects, methods for identifying an early indication, or methods for conducting a clinical trial where a functional biomarker is measured, the functional biomarker may be one or more of dark adaptation, low luminance visual acuity, low luminance deficit, contrast sensitivity, or scotopic sensitivity.

In the foregoing methods for selecting or identifying a subject, methods for stratifying a plurality of subjects, methods for identifying an early indication, or methods for conducting a clinical trials where the functional biomarker measured is dark adaptation, the subject value can be based on the rod intercept time, the rod-cone break time, the rod recovery slope, the time to scotopic threshold, or a combination of the foregoing.

In the foregoing methods for selecting or identifying a subject, methods for stratifying a plurality of subjects, methods for identifying an early indication, or methods for conducting a clinical trial the statin may be any statin approved for administration to the subject or undergoing evaluation for approval (such as in a clinical trial), including, but not limited to, atorvastatin (LIPITOR®), cerivastatin, fluvastatin (LESCOL®), lovastatin (MEVACOR®, ALTOCOR™), pitavastatin (LIVALO®), pravastatin (PRAVACHOL®, SELEKTINE®), rosuvastatin (CRESTOR®) simvastatin (ZOCOR®), analogs thereof, and combinations thereof.

In the foregoing methods for selecting or identifying a subject, methods for stratifying a plurality of subjects, methods for identifying an early indication, or methods for conducting a clinical trial, the statin may be atorvastatin (LIPITOR®).

In the foregoing methods for selecting or identifying a subject, methods for stratifying a plurality of subjects, methods for identifying an early indication, or methods for conducting a clinical trial where dark adaptation is measured any of the following conditions may be used:

- a 70% effective bleach and a 5° or 12° eccentricity test location;
- a 76% effective bleach and a 5° or 12° eccentricity test location;
- a 70% effective bleach and a 5° eccentricity test location;
- a 70% effective bleach and a 12° eccentricity test location;
- a 76% effective bleach and a 5° eccentricity test location; and
- a 76% effective bleach and a 12° eccentricity test location.

In any of the foregoing conditions, the 5° or 12° eccentricity test location may be centered on the inferior visual meridian.

In the foregoing methods for selecting or identifying a subject, methods for stratifying a plurality of subjects, methods for identifying an early indication, or methods for conducting a clinical trial where the rod intercept time is determined, the rod intercept criterion sensitivity level may be from $5\times10^{-2}$ scotopic cd/m$^2$ to $5\times10^{-4}$ scotopic cd/m$^2$. In any of the foregoing embodiments where the rod intercept time is determined, the rod intercept criterion sensitivity level may be $5\times10^{-3}$ scotopic cd/m$^2$.

Management of AMD Therapy

The disclosed functional biomarkers can also be used for management of AMD patients who are candidates for or who are using statin therapy. While statins are one of the most frequently prescribed drugs, their use has typically been the purview of cardiologists and internists attempting to lower cholesterol levels as a means for reducing the risk of cardiovascular diseases such as heart attacks and strokes. AMD is largely diagnosed and managed by eye care physicians such as ophthalmologists and optometrists who are in general not intimately familiar with administration of statins, the detailed physiological response, or the associated side effects. There is a need to provide tools for these eye care physicians to enable easy, effective management of statin therapy for AMD. The challenges faced by the physician include, for example, the uncertainly of whether a particular patient will respond or not, a long treatment duration (in some cases twelve months or more) before definitive structural indications of response are evident, and the risk of adverse side effects, some of which can be serious. Consequently, some patients may be exposed to prolonged risk before learning whether there is commensurate benefit. Thus, the disclosed functional biomarkers can be used, for example, to support treatment of AMD patients using statin therapy by, for example, identifying patients more likely to respond, providing an early indication of responders vs. non-responders, or demonstrating a treatment benefit, e.g., within 1, 2, 3, 4, 5, 6, 7, 8, 9, 10, 11, or 12 months of initiation of treatment.

In some methods, one or more of the functional biomarkers disclosed herein is measured at the initiation of therapy to provide a subject value that indicates the likelihood of a treatment effect or a baseline value to track treatment effect. In some embodiments, an impaired subject value indicates the potential for treatment response; for example, allowing the physician to decide whether the patient should be treated using a statin therapy. During or after administration of a statin treatment (e.g., at one or more of 1, 2, 3, 4, 5, 6, 8, 9, 10, 11, 12, 24, and/or 36 weeks, or 30, 60, 90, 180, 270 and/or 360 days, or 1, 2, 3, and/or 4 quarters after initiation of the treatment), the one or more functional biomarkers disclosed herein can be measured again to provide a subsequent value, and the subsequent value compared to the baseline value or an earlier subsequent value. In some embodiments, an improvement from the baseline value indicates that the therapy is effective or is likely to be effective for the patient. In some embodiments, no change or a worsening from the baseline value indicates that the therapy is ineffective or is likely to be ineffective for the patient; in this case, the treatment can, for example, be discontinued or the dose increased. In some embodiments, for example in patients who are expected to experience rapidly worsening disease based on medical history, no change from the baseline value can indicate that the therapy is effective or likely to be effective for the patient. In some embodiments, the disclosed functional biomarkers can be used to confirm a treatment benefit. Alternatively, these biomarkers can be used to identify patients more likely to respond to statin therapy or to provide an early indication of responders vs. non-responders.

In some embodiments, when deciding whether to treat a patient with statin therapy, those with an impaired functional biomarker (e.g., delayed dark adaptation or a larger than normal low luminance deficit) are more likely to respond to intervention, simply because they have deficits that can be corrected. In other embodiments, once treatment has started, improvement in a functional biomarker (e.g., a shortening of dark adaptation time or a lessening of low luminance deficit) is an early indicator of treatment efficacy and consequently indicates those more likely to have follow-on benefits such as disappearance of drusen or improvement in visual acuity.

As previously noted, it would be advantageous to limit the exposure to risks associated with statin therapy by identifying in advance those patients most likely to respond and by having a quick indication whether the treatment is having an effect after initiation. The risks associated with statin therapy generally fall into four categories (Golomb et al., 2008 *Am J Cardiovasc Drugs* 8(6):373-418):

Muscle Pain and Damage—The most common risk of statin therapy is mild to severe muscle pain. Very rarely (in a few cases per million), statin therapy is associated with rhabdomyolysis, a life-threatening muscle damage that can result in severe muscle pain, liver damage, kidney failure and even death.

Liver Damage—Statin therapy occasionally causes an increase in the level of enzymes that signal liver inflammation.

Increased Blood Glucose—There is a small risk of increased blood glucose that could lead to developing type 2 diabetes.

Neurological Side Effects—Some people have developed reversible memory loss or confusion while taking statins.

The risks of statin therapy are greatest for females, being age 65 or older, those having a smaller body frame, those having kidney or liver disease, and those taking multiple medications to lower cholesterol. In addition, numerous other drugs may interact adversely with statins, including amiodarone, gemfibrozil, protease inhibitors such as saquinavir and ritonavir, some antibiotics and antifungal medications such as clarithromycin and itraconazole, and some immunosuppressants such as cyclosporine.

Therefore, the following methods are provided in the present disclosure.

The present disclosure provides a method for determining or predicting efficacy of a treatment for AMD in a subject, wherein the treatment comprises administration of a statin. The method comprises the steps of: 1) optionally identifying the subject or having the subject identified as having AMD; 2) measuring or having measured one or more functional biomarkers in the subject; 3) determining or having determined a baseline value from the one or more measurements of step 2; 4) administering or continuing to administer a statin treatment to the subject; 5) measuring or having measured the one or more functional biomarkers in the subject at one or more second or later time points; 6) determining or having determined a corresponding subsequent value from the one or more measurements of step 5; and 7) optionally comparing the baseline value to the one or more corresponding subsequent values or comparing a subsequent value to an earlier subsequent value. In some embodiments where the treatment for AMD has the objective of preventing or delaying progression of AMD in the subject (for example, to prevent or delay atrophy of the RPE, to prevent or delay atrophy of one or more photoreceptors, to prevent or delay vision loss, and/or to prevent or delay progression from early AMD to advanced AMD), an improvement or no change in a subsequent value as compared to the baseline value (or a subsequent value as compared to an earlier subsequent value) indicates that the treatment is effective or likely to be effective in the subject. In some embodiments where the treatment for AMD has the objective of regression of AMD in the subject (for example, regression of drusen, regression of PEDs, and/or improvement in visual acuity)), a worsening or no change of a subsequent value as compared to the baseline value (or a subsequent value as compared to an earlier subsequent value) indicates that the treatment is ineffective or likely to be ineffective in the subject.

Such method may further comprise making a treatment decision based on the subject value and the baseline value (or the subsequent value and an earlier subsequent value). Such treatment decisions include: i) continuing the statin treatment without change; ii) continuing the statin treatment with an increase or decrease in the dose of the statin being administered (as compared to the initial dose); iii) continuing statin therapy with a different statin than initially administered (either at the same equivalent dose, a higher equivalent dose, or a lower equivalent dose); and iv) discontinuing statin treatment. In a specific embodiment, the treatment decision comprises or further comprises taking one of the following actions: i) continuing to treat the subject with the statin treatment at the initial statin dose (as compared to the initial statin dose) if the subsequent value is improved as compared to the baseline value (or an earlier subsequent value); ii) continuing to treat the subject with the statin treatment at the initial statin dose, continuing to treat the subject with the statin therapy at an increased or decreased statin dose (as compared to the initial statin dose), or continuing the statin therapy with a different statin if the subsequent value shows a change of less than 10% as compared to the baseline value (or an earlier subsequent value); or iii) discontinuing treating the subject with the statin treatment if the subsequent value shows a worsening of greater than or equal to 10% as compared to the baseline value (or an earlier subsequent value).

The present disclosure provides a method for determining or predicting efficacy of a treatment for AMD in a subject, wherein the treatment comprises administration of a statin. The method comprises the steps of: 1) optionally identifying the subject or having the subject identified as having AMD; 2) measuring or having measured dark adaptation in the subject; 3) determining or having determined the rod intercept time from the dark adaptation measurement to provide a baseline value; 4) administering or continuing to administer a statin treatment to the subject; 5) measuring or having measured dark adaptation in the subject at one or more second or later time points; 6) determining or having determined the rod intercept time from the dark adaptation measurement to provide a subsequent value; and 7) optionally comparing the baseline value to the one or more subsequent values or comparing a subsequent value to an earlier subsequent value. In some embodiments where the treatment for AMD has the objective of preventing or delaying progression of AMD in the subject (for example, to prevent or delay atrophy of the RPE, to prevent or delay atrophy of one or more photoreceptors, to prevent or delay vision loss, and/or to prevent or delay progression from early AMD to advanced AMD), an improvement or no change in a subsequent value as compared to the baseline value (or a subsequent value as compared to an earlier subsequent value) indicates that the treatment is effective or likely to be effective in the subject. In some embodiments where the treatment for AMD has the objective of regression of AMD in the subject (for example, regression of drusen, regression of PEDs, and/or improvement in visual acuity), a worsening or no change of a subsequent value as compared to the baseline value (or a subsequent value as compared to an earlier subsequent value) indicates that the treatment is ineffective or likely to be ineffective in the subject.

Such method may further comprise making a treatment decision based on the subject value and the baseline value (or the subsequent value and an earlier subsequent value). Such treatment decisions include: i) continuing the statin treatment without change; ii) continuing the statin treatment with an increase or decrease in the dose of the statin being administered (as compared to the initial dose); iii) continuing statin therapy with a different statin than initially administered (either at the same equivalent dose, a higher equivalent dose, or a lower equivalent dose); and iv) discontinuing statin treatment. In a particular embodiment, when the rod intercept time at a subsequent value is improved 180 seconds or more from the baseline value (or an earlier subsequent value), the treatment decision is to continue with the statin therapy without change or to decrease the dose of the statin. In a particular embodiment, when the change in rod intercept time at a subsequent value is improved or worsened less than 180 seconds from the baseline value (or an earlier subsequent value), the treatment decision is to continue with the statin therapy without change, continue the statin therapy with a different statin, continue the statin treatment with an increase in the dose of the statin being administered, continue the statin treatment with an increase in the dose of the statin being administered to 80 mg of atorvastatin daily or a dose equivalent to 80 mg of atorvastatin daily, or continue the statin treatment with an increase in the dose of the statin being administered to between 80 mg and 120 mg of atorvastatin daily or a dose equivalent to 80 mg to 120 mg of atorvastatin daily. In a particular embodiment, when the change in rod intercept time at a subsequent value is worsened 180 seconds or more from the baseline value (or an earlier subsequent value), the treatment decision is to discontinue treating the subject with the statin therapy.

The present disclosure provides a method for treating a subject with a statin, wherein the subject is suffering from AMD, the method comprising the steps of: 1) measuring or having measured one or more functional biomarkers in the subject; 2) determining or having determined a baseline value for the subject from the one or more measurements of step 1; 3) administering or continuing to administer a statin treatment to the subject at an initial statin dose; 4) measuring or having measured the one or more functional biomarkers in the subject at one or more second or later time points; 5) determining or having determined a subsequent value for the subject from the one or more measurements of step 4; and 6) making a treatment decision based on the subsequent value and the baseline value (or the subsequent value and an earlier subsequent value). Such treatment decisions includes: i) continuing the statin treatment without change; ii) continuing the statin treatment with an increase or decrease in the dose of the statin being administered (as compared to the initial dose); iii) continuing statin therapy with a different statin than initially administered (either at the same equivalent dose, a higher equivalent dose, or a lower equivalent dose); and iv) discontinuing statin treatment.

In a specific embodiment, the treatment decision comprises or further comprises taking one of the following actions: i) continuing to treat the subject with the statin treatment at the initial statin dose (as compared to the initial statin dose) if the subsequent value is improved as compared to the baseline value (or an earlier subsequent value); ii) continuing to treat the subject with the statin treatment at the initial statin dose, continuing to treat the subject with the statin therapy at an increased or decreased statin dose (as compared to the initial statin dose), or continuing the statin therapy with a different statin if the subsequent value shows a change of less than 10% as compared to the baseline value (or an earlier subsequent value); or iii) discontinuing treating the subject with the statin treatment if the subsequent value shows a worsening of greater than or equal to 10% as compared to the baseline value (or an earlier subsequent value).

In certain embodiments, the statin treatment is atorvastatin and the initial dose is from 40 mg to 120 mg daily. In certain embodiments, the statin therapy is cerivastatin, fluvastatin, lovastatin, pitavastatin, rosuvastatin, or simvastatin and the initial dose is from 40 mg dose equivalent to atorvastatin to 120 mg dose equivalent to atorvastatin daily. In certain embodiments, the increased statin dose is 1.5-fold to 10-fold the initial statin dose. In certain embodiments, the increased statin dose is 2-fold the initial statin dose. In certain embodiments, the increased statin dose is 80 mg of atorvastatin or a dose equivalent to 80 mg of atorvastatin daily. In certain embodiments, the increased statin dose is 80 mg to 120 mg of atorvastatin or a dose equivalent to 80 mg to 120 mg of atorvastatin daily.

The present disclosure provides a method for treating a subject with a statin, wherein the subject is suffering from AMD, the method comprising the steps of: 1) measuring or having measured dark adaptation in the subject; 2) determining or having determined a rod intercept time from the dark adaptation measurement to provide a baseline value; 3) administering or continuing to administer a statin treatment to the subject at an initial statin dose; 4) measuring or having measured dark adaptation in the subject at one or more second or later time points; 5) determining or having determined a rod intercept time from the dark adaptation measurement to provide a subsequent value; and 6) making a treatment decision based on the subsequent value and the baseline value (or the subsequent value and an earlier subsequent value). Such treatment decisions includes: i) continuing the statin treatment without change; ii) continuing the statin treatment with an increase or decrease in the dose of the statin being administered (as compared to the initial dose); iii) continuing statin therapy with a different statin than initially administered (either at the same equivalent dose, a higher equivalent dose, or a lower equivalent dose); and iv) discontinuing statin treatment.

In a specific embodiment, the treatment decision comprises or further comprises taking one of the following actions: i) when the rod intercept time at a subsequent value is improved 180 seconds or more from the baseline value (or an earlier subsequent value), the treatment decision is to continue with the statin therapy without change or continue with the statin therapy at a decreased dose (as compared to the initial dose); ii) when the rod intercept time at a subsequent value is improved or worsened less than 180 seconds from the baseline value (or an earlier subsequent value), the treatment decision is to continue with the statin therapy without change, continue the statin therapy with a different statin, continue the statin treatment with an increase or decrease in the dose of the statin being administered (as compared to the initial dose), continue the statin treatment with an increase in the dose of the statin being administered to 80 mg of atorvastatin daily or a dose equivalent to 80 mg of atorvastatin daily, or continue the statin treatment with an increase in the dose of the statin being administered to between 80 mg and 120 mg of atorvastatin daily or a dose equivalent to 80 mg to 120 mg of atorvastatin daily; or iii) when in rod intercept time at a subsequent value is worsened greater than 180 seconds from the baseline value (or an earlier subsequent value), the treatment decision is to discontinue treating the subject with the statin therapy.

In certain embodiments, the statin treatment is atorvastatin and the initial dose is from 40 mg to 120 mg daily. In certain embodiments, the statin therapy is cerivastatin, fluvastatin, lovastatin, pitavastatin, rosuvastatin, or simvastatin and the initial dose is from 40 mg dose equivalent to atorvastatin to 120 mg dose equivalent to atorvastatin daily. In certain embodiments, the increased statin dose is 1.5-fold to 10-fold the initial statin dose. In certain embodiments, the increased statin dose is 2-fold the initial statin dose. In certain embodiments, the increased statin dose is 80 mg of atorvastatin or a dose equivalent to 80 mg of atorvastatin daily. In certain embodiments, the increased statin dose is 80 mg to 120 mg of atorvastatin or a dose equivalent to 80 mg to 120 mg of atorvastatin daily.

The present disclosure provides a method for treating a subject with a statin, wherein the subject is suffering from AMD, the method comprising the steps of: 1) measuring or having measured dark adaptation in the subject; 2) determining or having determined a rod intercept time from the dark adaptation measurement to provide a baseline value; 3) administering or continuing to administer a statin treatment to the subject at an initial statin dose; 4) measuring or having measured dark adaptation in the subject at one or more second or later time points; 5) determining or having determined a rod intercept time from the dark adaptation measurement to provide a subsequent value; and 6) continuing to treat the subject with the statin treatment at the initial statin dose or at a decreased statin dose if the rod intercept time is improved 180 seconds or more from the baseline value (or an earlier subsequent value). In certain embodiments, the statin treatment is atorvastatin and the initial statin dose is from 40 mg to 120 mg daily. In certain embodiments, the statin therapy is cerivastatin, fluvastatin, lovastatin, pitavastatin, rosuvastatin, or simvastatin and the initial statin dose is from 40 mg dose equivalent to atorvastatin to 120 mg dose equivalent to atorvastatin daily.

In certain embodiments, the statin treatment is atorvastatin and the initial dose is from 40 mg to 120 mg daily. In certain embodiments, the statin therapy is cerivastatin, fluvastatin, lovastatin, pitavastatin, rosuvastatin, or simvastatin and the initial dose is from 40 mg dose equivalent to atorvastatin to 120 mg dose equivalent to atorvastatin daily. In certain embodiments, the increased statin dose is 1.5-fold to 10-fold the initial statin dose. In certain embodiments, the increased statin dose is 2-fold the initial statin dose. In certain embodiments, the increased statin dose is 80 mg of atorvastatin or a dose equivalent to 80 mg of atorvastatin daily. In certain embodiments, the increased statin dose is 80 mg to 120 mg of atorvastatin or a dose equivalent to 80 mg to 120 mg of atorvastatin daily.

The present disclosure provides a method for treating a subject with a statin, wherein the subject is suffering from AMD, the method comprising the steps of: 1) measuring or having measured dark adaptation in the subject; 2) determining or having determined a rod intercept time from the dark adaptation measurement to provide a baseline value; 3) administering or continuing to administer a statin treatment to the subject at an initial statin dose; 4) measuring or having measured dark adaptation in the subject at one or more second or later time points; 5) determining or having determined a rod intercept time from the dark adaptation measurement to provide a subsequent value; and 6) continuing to treat the subject with the statin treatment at an initial statin dose, continuing to treat the subject with the statin therapy at an increased statin dose (as compared to the initial statin dose), or continuing the statin therapy with a different statin if the rod intercept time is improved or worsened less than 180 seconds from the baseline value (or an earlier subsequent value). In certain embodiments, the increased statin dose is 1.5-fold to 10-fold the initial statin dose. In certain embodiments, the increased statin dose is 2-fold the initial statin dose. In certain embodiments, the increased statin dose is 80 mg of atorvastatin or a dose equivalent to 80 mg of atorvastatin daily. In certain embodiments, the increased statin dose is 80 mg to 120 mg of atorvastatin or a dose equivalent to 80 mg to 120 mg of atorvastatin daily.

In certain embodiments, the statin treatment is atorvastatin and the initial dose is from 40 mg to 120 mg daily. In certain embodiments, the statin therapy is cerivastatin, fluvastatin, lovastatin, pitavastatin, rosuvastatin, or simvastatin and the initial dose is from 40 mg dose equivalent to atorvastatin to 120 mg dose equivalent to atorvastatin daily. In certain embodiments, the increased statin dose is 1.5-fold to 10-fold the initial statin dose. In certain embodiments, the increased statin dose is 2-fold the initial statin dose. In certain embodiments, the increased statin dose is 80 mg of atorvastatin or a dose equivalent to 80 mg of atorvastatin daily. In certain embodiments, the increased statin dose is 80 mg to 120 mg of atorvastatin or a dose equivalent to 80 mg to 120 mg of atorvastatin daily.

The present disclosure provides a method for treating a subject with a statin, wherein the subject is suffering from AMD, the method comprising the steps of: 1) measuring or having measured dark adaptation in the subject; 2) determining or having determined a rod intercept time from the dark adaptation measurement to provide a baseline value; 3) administering or continuing to administer a statin treatment to the subject at an initial statin dose; 4) measuring or having measured dark adaptation in the subject at one or more second or later time points; 5) determining or having determined a rod intercept time from the dark adaptation measurement to provide a subsequent value; and 6) discontinuing treating the subject with the statin treatment if the rod intercept time is worsened 180 seconds or more from the baseline value (or an earlier subsequent value).

In certain embodiments, the statin treatment is atorvastatin and the initial dose is from 40 mg to 120 mg daily. In certain embodiments, the statin therapy is cerivastatin, fluvastatin, lovastatin, pitavastatin, rosuvastatin, or simvastatin and the initial dose is from 40 mg dose equivalent to atorvastatin to 120 mg dose equivalent to atorvastatin daily. In certain embodiments, the increased statin dose is 1.5-fold to 10-fold the initial statin dose. In certain embodiments, the increased statin dose is 2-fold the initial statin dose. In certain embodiments, the increased statin dose is 80 mg of atorvastatin or a dose equivalent to 80 mg of atorvastatin daily. In certain embodiments, the increased statin dose is 80 mg to 120 mg of atorvastatin or a dose equivalent to 80 mg to 120 mg of atorvastatin daily.

The present disclosure also provides a method of selecting a subject for treatment with a statin therapy, wherein the subject is suffering from AMD, the method comprising the steps of: 1) measuring or having measured one or more functional biomarkers in the subject; 2) determining or having determined a subject value for the subject from the one or more measurements of step 1; 3) comparing the subject value to a corresponding reference range; and 4) selecting the subject for treatment with the statin therapy if the subject value falls within the reference range or not selecting the subject for treatment with the statin therapy if the subject value falls outside the reference range. In certain embodiments, the statin therapy is atorvastatin and the dose is from 40 mg to 120 mg daily. In certain embodiments, the statin therapy is cerivastatin, fluvastatin, lovastatin, pitavastatin, rosuvastatin, or simvastatin and the dose is a dose equivalent to 40 mg to 120 mg of atorvastatin daily.

The present disclosure also provides a method of selecting a subject for treatment with a statin therapy, wherein the subject is suffering from AMD, the method comprising the steps of: 1) measuring or having measured dark adaptation in the subject; 2) determining or having determined the rod intercept time from the dark adaptation measurement to provide a subject value; 3) comparing the subject value to a corresponding reference range; and 4) selecting the subject for treatment with the statin therapy if the subject value falls within the reference range or not selecting the subject for treatment with the statin therapy if the subject value falls outside the reference range. In certain embodiments, the statin therapy is atorvastatin and the dose is from 40 mg to 120 mg daily. In certain embodiments, the statin therapy is cerivastatin, fluvastatin, lovastatin, pitavastatin, rosuvastatin, or simvastatin and the dose is a dose equivalent to 40 mg to 120 mg of atorvastatin daily.

I In any of the foregoing methods of determining or predicting efficacy, methods of treatment, or methods of selection, the statin may be any statin approved for administration to the subject or undergoing evaluation for approval (such as in a clinical trial), including, but not limited to, atorvastatin (LIPITOR®), cerivastatin, fluvastatin (LESCOL®), lovastatin (MEVACOR®, ALTOCOR™), pitavastatin (LIVALO®), pravastatin (PRAVACHOL®, SELEKTINE®), rosuvastatin (CRESTOR®) simvastatin (ZOCOR®), analogs thereof, and combinations thereof.

In any of the foregoing methods of determining or predicting efficacy, methods of treatment, or methods of selection where dark adaptation is measured any of the following conditions may be used:

- a 70% effective bleach and a 5° or 12° eccentricity test location;
- a 76% effective bleach and a 5° or 12° eccentricity test location;
- a 70% effective bleach and a 5° eccentricity test location;
- a 70% effective bleach and a 12° eccentricity test location;
- a 76% effective bleach and a 5° eccentricity test location; and
- a 76% effective bleach and a 12° eccentricity test location.

In any of the foregoing conditions, the 5° or 12° eccentricity test location may be centered on the inferior visual meridian.

In any of the foregoing methods of determining or predicting efficacy, methods of treatment, or methods of selection where the rod intercept time is determined, the rod intercept criterion sensitivity level may be from $5\times10^{-2}$ scotopic cd/$m^2$ to $5\times10^{-4}$ scotopic cd/$m^2$. In any of the foregoing embodiments where the rod intercept time is determined, the rod intercept criterion sensitivity level may be $5\times10^{-3}$ scotopic cd/$m^2$.

In any of the foregoing methods of determining or predicting efficacy, methods of treatment, or methods of selection, the methods of treatment may have the objective of regressing drusen (e.g., soft drusen), regressing PEDs, preventing or delaying atrophy of the RPE, preventing or delaying atrophy of one or more photoreceptors, preventing or delaying vision loss, improving vision (e.g., visual acuity), and/or preventing or delaying progression from early AMD to advanced AMD (e.g., geographic atrophy or choroidal neovascularization).

In any of the foregoing methods of determining or predicting efficacy, methods of treatment, or methods of selection, the subjects may have soft drusen. In any of the foregoing methods of treatment, the subjects may be determined after clinical assessment to have early AMD. In any of the foregoing methods of treatment, the subjects may be determined after clinical assessment to have intermediate AMD. In any of the foregoing methods of treatment, the subjects may have SDDs.

In any of the foregoing methods of determining or predicting efficacy, methods of treatment, or methods of selection, the baseline value may be determined prior to the initiation of statin treatment or concurrently with the initiation of statin treatment. In any of the foregoing methods of treatment or methods of selection, a subsequent value may be taken 1 month or greater from the baseline value or an earlier subsequent value. In any of the foregoing methods of treatment or methods of selection, a subsequent value may be taken 3 months or greater from the baseline value or an earlier subsequent value. In any of the foregoing methods of treatment or methods of selection, a subsequent value may be taken 6 months or greater from the baseline value or an earlier subsequent value. In any of the foregoing methods of treatment or methods of selection, a subsequent value may be taken 12 months or greater from the baseline value or an earlier subsequent value.

Statins

The methods described herein include administration of high-dose statins, for example as described in international patent application WO 2017/066529. Statins (or HMG-CoA reductase inhibitors) are a class of cholesterol lowering drugs that are similar in structure to HMG-CoA, shown below:

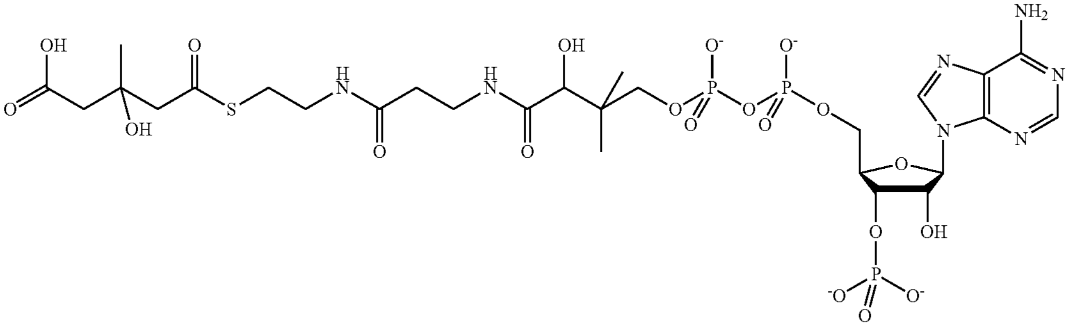

Statins inhibit the enzyme HMG-CoA reductase by competitively binding to HMG-CoA reductase in the HMG-CoA active site. Any statin may be used in connection with the methods described herein. Non-limiting examples of statins include: atorvastatin (LIPITOR®), cerivastatin, fluvastatin (LESCOL®), lovastatin (MEVACOR®, ALTOCOR™), pitavastatin (LIVALO®), pravastatin (PRAVACHOL®, SELEKTINE®), rosuvastatin (CRESTOR®) simvastatin (ZOCOR®), analogs thereof, and combinations thereof. In some embodiments, the statin used in a method described herein is atorvastatin.

Statins can be either lipophilic or hydrophilic. Lipophilic statins include, for example, atorvastatin, lovastatin, and simvastatin. Hydrophilic statins include, for example, fluvastatin, rosuvastatin, and pravastatin. In some embodiments, the statin used in a method described herein is lipophilic (e.g., atorvastatin).

As used herein the term "high-dose" refers to any dose that exceeds the defined daily dose (DDD) according to the World Health Organization (WHO). The 2015 ATC/DDD Index indicates the DDD as 20 mg for atorvastatin, 0.2 mg for cerivastatin, 60 mg for fluvastatin, 45 mg for lovastatin, 2 mg for pitavastatin, 30 mg for pravastatin, 10 mg for rosuvastatin, and 30 mg for simvastatin (see, e.g., whocc.no/atc_ddd_index/). For example, in embodiments where the statin used in a method described herein is atorvastatin (having a DDD of 20 mg), a high-dose of atorvastatin can be at least 40 mg, at least 50 mg, at least 60 mg, at least 70 mg, at least 80 mg, at least 90 mg, at least 100 mg, at least 120 mg, at least 140 mg, or at least 160 mg. In some embodiments, the dose used is at least 80 mg for atorvastatin (e.g., 80-100, 80-120, 80-140, or 80-160 mg).

In other embodiments, where the statin used in a method described herein is a statin other than atorvastatin, a dose equivalent of high-dose atorvastatin can be used. Equivalent doses of other statins can be easily determined by a skilled person. For example, based on the DDD of the statins, an equivalent dose of 80 mg atorvastatin could be 0.8 mg for cerivastatin, 240 mg for fluvastatin, 180 mg for lovastatin, 8 mg for pitavastatin, 120 mg for pravastatin, 40 mg for rosuvastatin, and 120 mg for simvastatin. In some embodiments, the dose used is at least 0.8 mg for cerivastatin (e.g., 0.8-1.0, 0.8-1.2, 0.8-1.4, or 0.8-1.6 mg); at least 80 mg for fluvastatin (e.g., 80-100, 80-120, 80-140, or 80-160 mg); at least 80 mg for lovastatin (e.g., 80-100, 80-120, 80-140, or 80-160 mg); at least 4 mg for pitavastatin (e.g., 4-6, 4-8, or 4-10 mg); at least 40 mg for pravastatin (e.g., 40-50, 40-60, 40-70, or 40-80 mg); at least 40 mg for rosuvastatin (e.g., 40-50, 40-60, 40-70, or 40-80 mg); and at least 80 mg for simvastatin (e.g., 80-100, 80-120, 80-140, or 80-160 mg).

Also provided herein are methods that include administration of maintenance-dose statins. For example, following effective treatment of AMD, the amount of statin administered can be reduced from a high-dose statin to a maintenance-dose statin. As used herein a "maintenance dose" is lower than the high-dose and indicates a dose of statin that is about equal to the DDD according to the WHO of a statin. For example, a maintenance dose of atorvastatin (having a DDD of 20 mg) can be about 15 mg, about 20 mg, about 25 mg, about 30 mg, about 35 mg, about 40 mg, about 45 mg, about 50 mg, about 55 mg, or about 60 mg. In some embodiments, a maintenance-dose statin is about 60 mg atorvastatin. In some embodiments, a maintenance-dose statin is about 40 mg atorvastatin.

In other embodiments, where the statin used in a method described herein is a statin other than atorvastatin, a dose equivalent of maintenance-dose atorvastatin can be used. Equivalent doses of other statins can be easily determined by a skilled person. For example, based on the DDD of the statins, an equivalent maintenance-dose of 40 mg atorvastatin could be 0.4 mg for cerivastatin, 120 mg for fluvastatin, 90 mg for lovastatin, 4 mg for pitavastatin, 60 mg for pravastatin, 20 mg for rosuvastatin, and 60 mg for simvastatin.

In some embodiments, the statin is administered systemically, e.g., orally or parenterally. If not otherwise specified herein, a recited dose of a statin will be understood to be a daily dose.

1. EXAMPLES

The invention is further described in the following examples, which do not limit the scope of the invention described in the claims.

Example 1—Improvement in Contrast Sensitivity After Initiation of Statin Treatment An adult female patient having intermediate AMD was treated with oral atorvastatin at doses increasing to 80 mg per day over six months. The patient was asked to report any perceived changes in visual function during the course of the treatment. The patient, an artist, self-reported improvement in contrast sensitivity after initiation of the treatment. This self-reported improvement in contrast sensitivity occurred well in advance of eventual resolution of the drusen associated with her AMD. No objective testing was done to document the improvement in contrast sensitivity. However, as an artist this patient was keenly aware of her visual functions, so her self-reported improvement in contrast sensitivity had substantial credence.

Example 2—Improvement in Dark Adaptation Precedes Drusen Resolution After Statin Treatment An adult male patient having intermediate AMD was treated with oral atorvastatin for 23 months according to the following schedule.

| | |
|---|---|
| Month 1 | 10 mg per day |
| Month 2 | 20 mg per day |
| Month 3 | 40 mg per day |
| Months 4 through 7 | 60 mg per day |
| Months 8 through 23 | 80 mg per day |

The patient was asked to report any perceived changes in visual function during the course of the treatment. The patient, a professional photographer, self-reported improvement in dark adaptation at month 7 of treatment. The self-reported improvement was confirmed at months 15 and 22 of treatment. In addition, at month 15 of treatment an ophthalmic examination of the patient indicated substantially complete resolution of the drusen associated with his AMD. The resolution of the drusen was confirmed by fundus photography and optical coherence tomography (OCT) imaging. The self-reported improvement in dark adaptation (first reported at month 7) occurred well in advance of clinically evident reduction in drusen load (first determined at month 15). No objective testing was done to document the improvement in dark adaptation. However, as a professional photographer, this patient was keenly aware of his visual function—in particular his ability to make transitions from light to darkness when entering his photographic dark room to develop film—so his self-reported improvement in dark adaptation had substantial credence.

Example 3—Changes in Dark Adaptation Parameters Are Indicative of Clinical Outcome in AMD Patients Undergoing Statin Treatment Dark adaptation data, and optionally other visual function data, was collected for a case series of seven AMD patients being treated with statin therapy. Table 1 shows demographic information for the seven patients and details regarding their statin therapy.

TABLE 1

| Patient | Sex | Date of Birth | Statin | Dose (mg/day) | Start Date |
|---|---|---|---|---|---|
| 1 | M | Feb. 11, 1938 | atorvastatin | 20 to 80 | July 2013 |
| 2 | F | Apr. 8, 1946 | atorvastatin | 80 | January 2013 |
| 3 | M | Jan. 20, 1939 | atorvastatin | 80 | October 2016 |
| 4 | F | Feb. 11, 1947 | atorvastatin | 80 | May 2018 |
| 5 | F | Apr. 28, 1943 | atorvastatin | 80 | January 2014* |
| | | | atorvastatin | 20 | February 2016 |
| | | | pravastatin | 20 | April 2018 |
| 6 | F | May 10, 1952 | atorvastatin | 80 | November 2017 |
| 7 | M | Apr. 11, 1942 | atorvastatin | 10 to 20 | April 2016 |

*Patient 5 suspended statin therapy between January 2015 and February 2016

Drusen, along with other structural features such as PEDs and pigmentary changes, have been used by clinicians as one indicator of AMD and its progression or regression. The presence of drusen per se does not directly interfere with dark adaptation or other visual functions in a significant way. However, as previously explained, the BlinD and BlamD that form on BM as precursors to development of drusen can act as a transport barrier between the RPE and choroid, impeding the supply of oxygen and nutrients coming from the choroid to the RPE and the removal of waste products going the opposite direction. This transport barrier can disrupt the visual cycle and thereby have a dramatic negative affect on dark adaptation parameters, including the rod intercept time (also referred to as RI time or RI value). Since lipids are a major component of Bind) and BlamD, therapies such as the administration of statins drugs that have the ability to affect lipid accumulation and/or distribution may be able to decrease and/or regress drusen and the underlying BlinD and. BlamD accumulation. Since BlinD and BlamD can impact dark adaptation parameters, including the RI time, dark adaptation parameters, including, but not limited to, the RI time, have the ability to serve as functional biomarkers for AMD and its progression or regression. Furthermore, the use of dark adaptation parameters, including, but not limited to the RI time, is also linked to the mechanisms of action of statin therapy. Consequently, the use of a dark adaptation parameter, such as, but not limited to, the RI time, as a functional biomarker for AMD in patients undergoing statin therapy relics, at least in part, on different physiological processes and manifestations than other biomarkers for AMD, such as but not limited to, drusen, PEDs, and pigmentary changes.

Table 2 provides detailed information regarding patients 1 to 7, including the baseline diagnosis (diagnosis made when starting statin therapy), ending diagnosis (the diagnosis made on the date of the last referenced evaluation), the results of evaluations performed on each patient, and whether the patient responded to statin therapy. The dark adaptation data in this Example is the rod intercept time (or RI time) reported in minutes. In this Example, the dark adaptation data was collected using the AdaptDx® Dark Adaptometer (MacuLogix, Middletown, PA) running its standard Extended Test protocol. The Extended Test protocol employs a 76% effective bleach and a test location of 5° eccentricity on the inferior visual meridian. Data is automatically analyzed by the AdaptDx Dark Adaptometer to provide an RI time based on recovery to a criterion sensitivity level of $5\times10^{-3}$ scotopic cd/m$^2$. A value of >20 minutes indicates that an RI time could not be determined for that patient at the expiration of 20 minutes of testing. The visual acuity data was collected using a standard Snellen or ETDRS eye chart with the results presented using the standard 20/20 vision scale. Drusen resolution was determined by evaluation of fundus and OCT imaging by qualified clinicians experienced in AMD evaluation. Fundus and OCT imaging data was collected using the Heidelberg Engineering Spectralis® SD-OCT (Heidelberg, Germany) or the Karl Zeiss Meditec Cirrus® HD-OCT (Jena, Germany), in both cases running standard protocols with automated data analysis performed by the instruments.

TABLE 2

| | Date | Month | OD | OS | Responder |
|---|---|---|---|---|---|
| Patient #1 | July 2013 | 0 | Intermediate AMD | Intermediate AMD | |
| | July 2013 | 0 | VA 20/25 | VA 20/32 | |
| | July 2015 | 24 | RI > 20 | RI = 17.13 | |
| | June 2018 | 59 | VA 20/25 | VA 20/25 | |
| | June 2018 | 59 | No indication of drusen resolution OU | | |
| | July 2018 | 60 | RI > 20 | RI > 20 | |
| | July 2018 | 60 | Intermediate AMD | Intermediate AMD | No |
| Patient #2 | January 2013 | 0 | Intermediate AMD | Intermediate AMD | |
| | January 2015 | 24 | RI = 18.72 | RI = 9.88 | |
| | December 2015 | 35 | Substantially complete drusen resolution | | |
| | December 2015 | 35 | Decrease in retina volume of 0.26 mm$^3$ | | |
| | August 2016 | 43 | | Substantially complete drusen resolution | |
| | August 2016 | 43 | | Decrease in retina volume of 0.25 mm$^3$ | |
| | May 2018 | 64 | VA 20/30 | VA 20/20 | |
| | July 2018 | 66 | RI = 17.05 | RI = 7.28 | |
| | July 2018 | 66 | Early AMD | Early AMD | Yes |
| Patient #3 | October 2016 | 0 | Late AMD (CNV) | Intermediate AMD w/SDD | |
| | June 2017 | 8 | RI > 20 | RI > 20 | |
| | May 2018 | 19 | No indication of SDD resolution OU | | |
| | June 2018 | 20 | RI > 20 | RI > 20 | |
| | June 2018 | 20 | Late AMD (CNV) | Intermediate AMD w/SDD | No |
| Patient #4 | May 2018 | 0 | Late AMD (GA) | Intermediate AMD | |
| | May 2018 | 0 | VA 20/200 | VA 20/20 | |
| | May 2018 | 0 | RI > 20 | RI > 20 | |
| | August 2018 | 3 | VA 20/200 | VA 20/20 | |
| | August 2018 | 3 | No indication of drusen resolution OU | | |
| | September 2018 | 4 | RI > 20 | RI > 20 | |
| | September 2018 | 4 | Late AMD (GA) | Intermediate AMD | No |

TABLE 2-continued

| | Date | Month | OD | OS | Responder |
|---|---|---|---|---|---|
| Patient #5 | January 2014 | 0 | Intermediate AMD | Intermediate AMD | |
| | January 2014 | 0 | VA 20/25 | VA 20/25 | |
| | October 2015 | 21 | RI = 9.68 | RI = 11.04 | |
| | April 2018 | 51 | No indication of drusen resolution OU | | |
| | June 2018 | 52 | RI = 17.19 | RI = 10.81 | |
| | June 2018 | 52 | Intermediate AMD | Intermediate AMD | No |
| Patient #6 | August 2017 | −3 | RI = 5.75 | NM | |
| | November 2017 | 0 | Intermediate AMD | Intermediate AMD | |
| | August 2018 | 9 | RI = 2.55 | NM | |
| | August 2018 | 9 | Initial signs of drusen resolution OU | | |
| | August 2018 | 9 | Decrease in retina volume of 0.09 $mm^3$ | Decrease in retina volume of 0.1 $mm^3$ | |
| | August 2018 | 9 | Intermediate AMD | Intermediate AMD | Maybe |
| Patient #7 | April 2016 | 0 | Intermediate AMD | Intermediate AMD | |
| | April 2016 | 0 | RI > 20 | RI > 20 | |
| | July 2018 | 27 | RI > 20 | RI > 20 | |
| | July 2018 | 27 | No indication of drusen resolution OU | | |
| | July 2018 | 27 | Intermediate AMD | Intermediate AMD | No |

The baseline diagnosis and ending diagnosis are the result of clinical assessment by qualified clinicians experienced in evaluation of AMD patients. The clinical assessment was carried out utilizing standard ophthalmic testing, such as, but not limited to, slit-lamp biomicroscopy (including looking for evidence of drusen and pigmentary changes), fundus and OCT imaging (including looking for evidence of drusen and pigmentary changes and calculation of retinal volume and retinal thickness), and testing with a Snellen or ETDRS eye chart (including looking for visual acuity changes that might indicate a change in disease status). Dark adaptation results were not used in the clinical assessment of the baseline or ending diagnosis.

As can be seen from the data in Table 2, RI time was a robust predictor for efficacy of statin treatment in patients with AMD, in particular patients with intermediate AMD. Patients 1, 3-5 and 7 were determined to be non-responders to statin treatment as the initial diagnosis was unchanged after treatment and clinical evaluation. For these patients, RI time either showed no improvement/essentially no improvement (patient 1 OD; patient 3 OU; patient 4 OU; patient 5 OS; and patient 7 OU) or got worse (patient 1 OS; and patient 5 OD), agreeing with the clinical assessment of not responding (i.e., not improving clinically). Patient 2 was determined to be a responder to statin therapy as the initial diagnosis improved after treatment (initial diagnosis intermediate AMD OU; ending diagnosis early AMD OU). For patient 2, RI time improved by 1.67 minutes OD and 2.60 minutes OS agreeing with the clinical assessment of a response to statin therapy (i.e., improving clinically). Patient 6 could not be clearly classified as a responder or non-responder to statin treatment. While the initial diagnosis was still unchanged after treatment and clinical evaluation, patient 6 displayed signs of drusen resolution and a small decrease in retinal volume after only nine months of therapy, indicating the possible beginning of treatment efficacy. For patient 6, RI time decreased by 2.2 minutes OD, agreeing with the initial clinical signs of a response to statin therapy.

The results from patients 2, 5, 6, and 7 are discussed in more detail below.

Patient 2

Figure 4A:
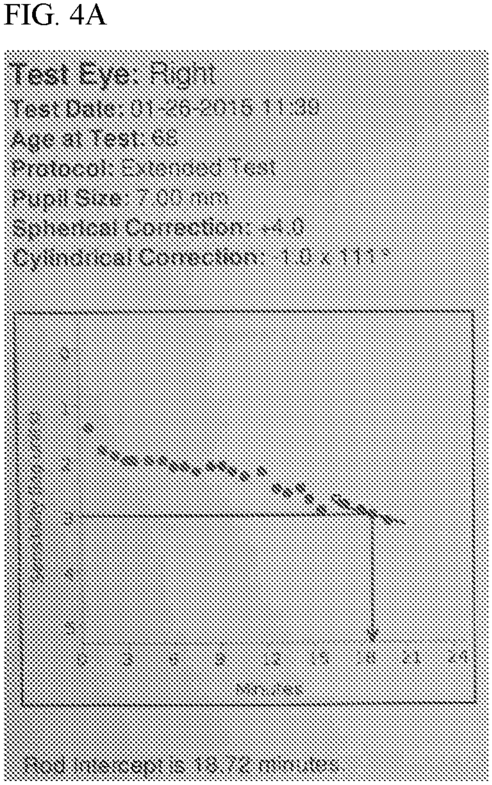
FIG. 4A shows dark adaptation results for patient 2 (OD). The date of the test was 1-26-15 and the patient was 68 years of age on the test date. Pupil size was 7.00 mm. A spherical correction of +4.0 and a cylindrical correction of −1.0×111° was used. The RI time was determined to be 18.72 min.
Figure 4B:
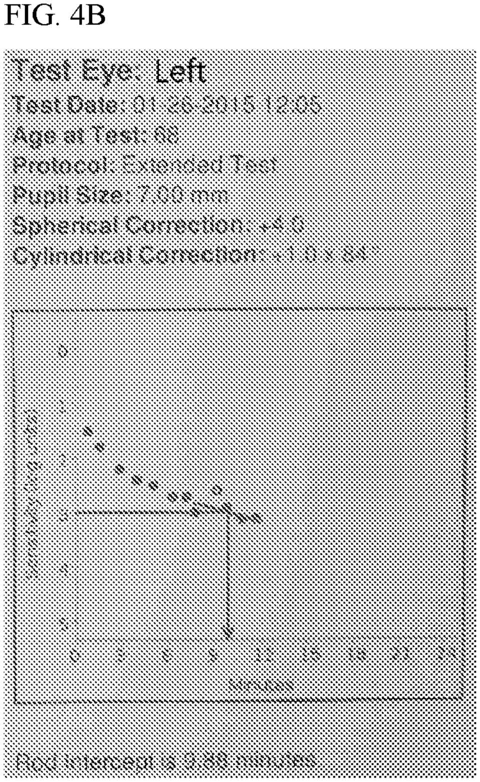
FIG. 4B shows dark adaptation results for patient 2 (OS). The details are the same as in FIG. 4A, with the exception a cylindrical correction of +1.0×84° was used. The RI time was determined to be 9.88 min.

After clinical assessment, patient 2 was diagnosed with intermediate AMD (both eyes, OU). Patient 2 initiated statin therapy with atorvastatin (80 mg per day) in January 2013. In January 2015, patient 2 underwent dark adaptation testing as described above. The results are shown in FIGS. 4A (right eye, OD) and 4B (left eye, OS). The RI times were determined to be 18.72 minutes OD and 9.88 minutes OS.

Figure 3A:
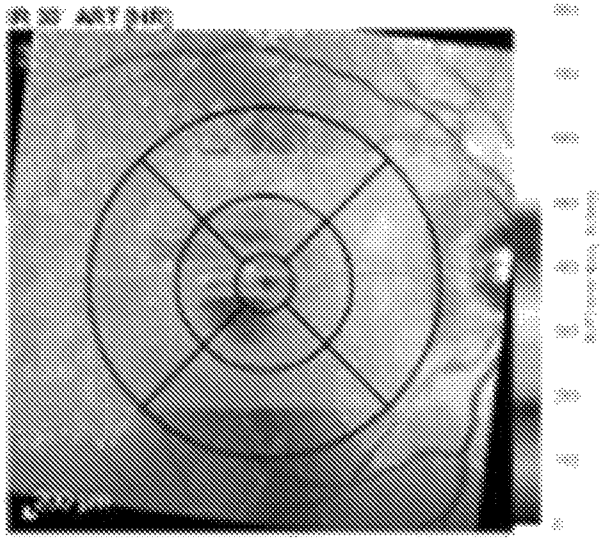
FIG. 3A shows representative fundus photography for patient 2 (OD) (test date 8-11-15).
Figure 3B:
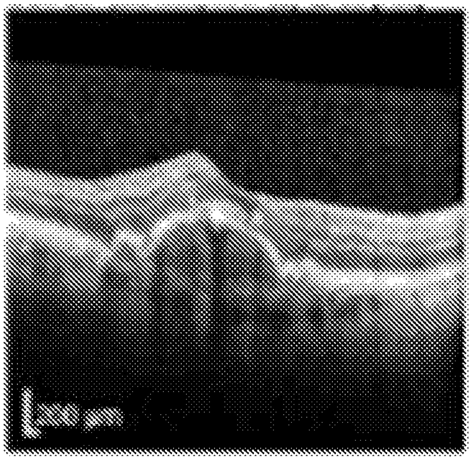
FIG. 3B shows representative OCT retinal imaging for patient 2 (OD) (test date 8-11-15).
Figure 3C:
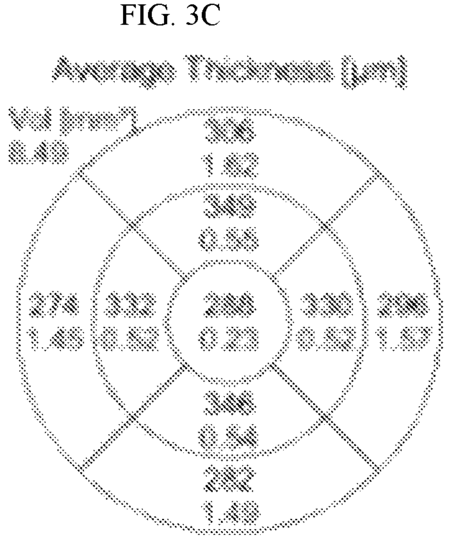
FIG. 3C shows the average thickness (in μM) and average volume ($mm^3$) of the retina as derived from the OCT imaging of FIG. 3B.
Figure 3D:
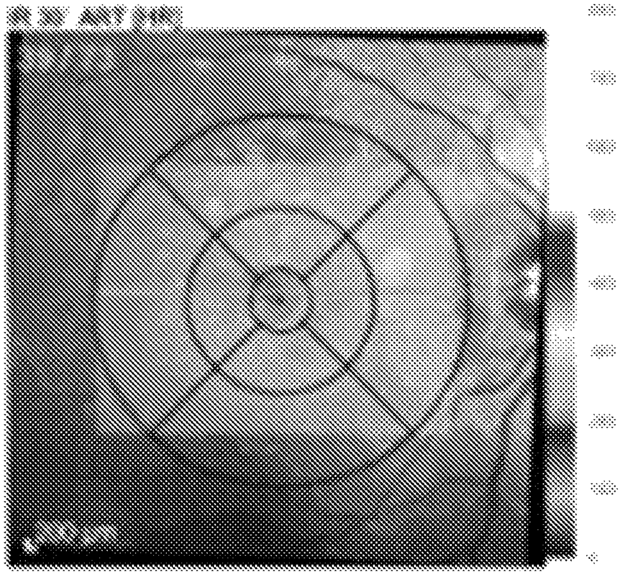
FIG. 3D shows representative fundus photography for patient 2 (OD) (test date 12-22-15).
Figure 3E:
FIG. 3E shows representative OCT retinal imaging for patient 2 (OD) (test date 12-22-15).
Figure 3F:
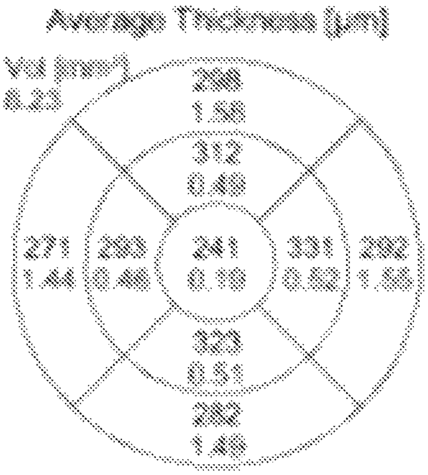
FIG. 3F shows the average thickness (in μM) and average volume ($mm^3$) of the retina as derived from the OCT imaging of FIG. 3E.
Figure 3G:
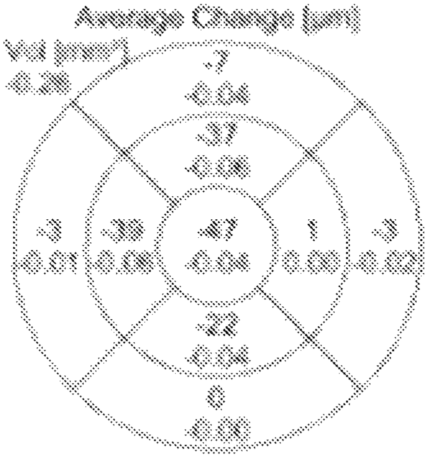
FIG. 3G shows the average change in average thickness (in μM) and average volume ($mm^3$) of the retina as derived from the data in FIGS. 3C and 3F.

Patient 2 underwent OCT retinal imaging for the right eye as described above in August and December of 2015. OCT images from the August 2015 test are shown in FIGS. 3A and 3B. FIG. 3C shows average retinal thickness (μM) and average retinal volume ($mm^3$) for the ETDRS segments as determined from analysis of the August 2015 OCT images (using standard software of the OCT imaging system). Average retinal thickness was determined to be 179 μM (minimum of 176 μM and maximum of 461 μM) and average total volume was determined to be 8.49 $mm^3$. OCT images from the December 2015 test are shown in FIGS. 3D and 3E. FIG. 3F shows average retinal thickness (W) and average retinal volume ($mm^3$) for the ETDRS segments as determined from analysis of the December 2015 OCT images (using standard software of the OCT imaging system). Average retinal thickness was determined to be 199 μM (minimum of 170 μM and maximum of 332 μM) and average total volume was determined to be 8.23 $mm^3$. FIG. 3G shows the average change between August 2015 and December 2015 in retinal thickness and volume over the ETDRS segments. The data show a rapid, substantially complete drusen resolution and an overall decrease in retinal volume of 0.26 $mm^3$.

Figure 3H:
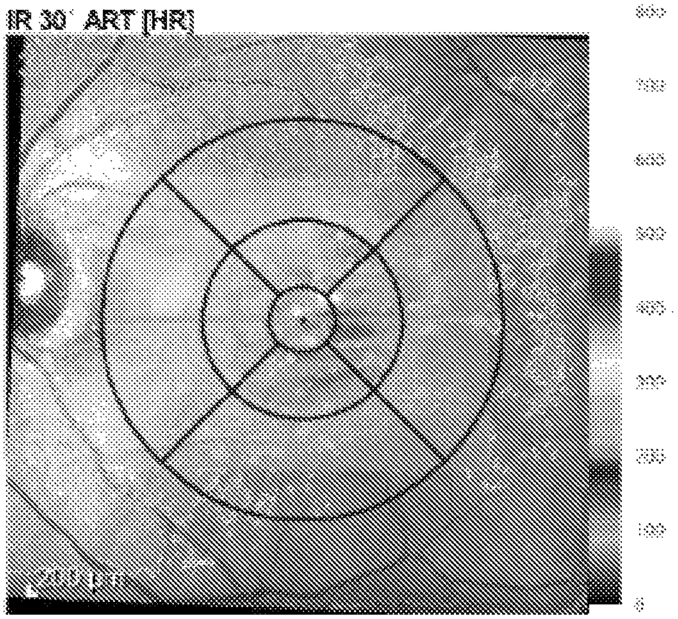
FIG. 3H shows representative fundus photography for patient 2 (OS) (test date 2-12-16).
Figure 3I:
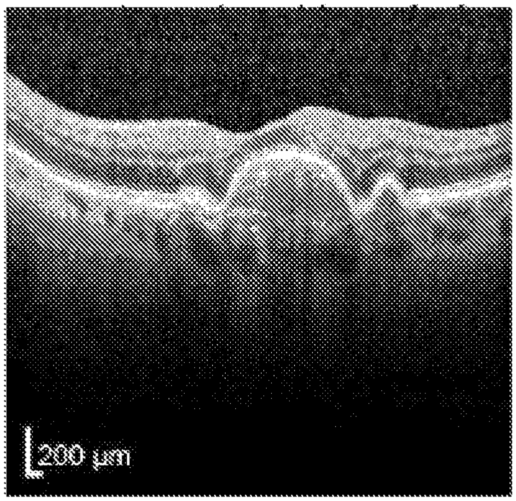
FIG. 3I shows representative OCT retinal imaging for patient 2 (OS) (test date 2-12-16).
Figure 3J:
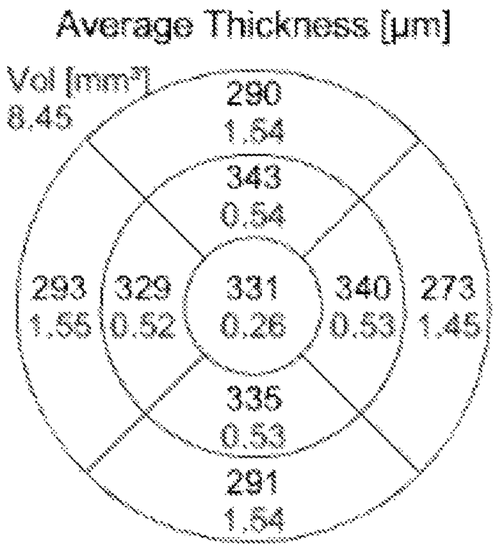
FIG. 3J shows the average thickness (in μM) and average volume ($mm^3$) of the retina as derived from the OCT imaging of FIG. 3I.
Figure 3K:
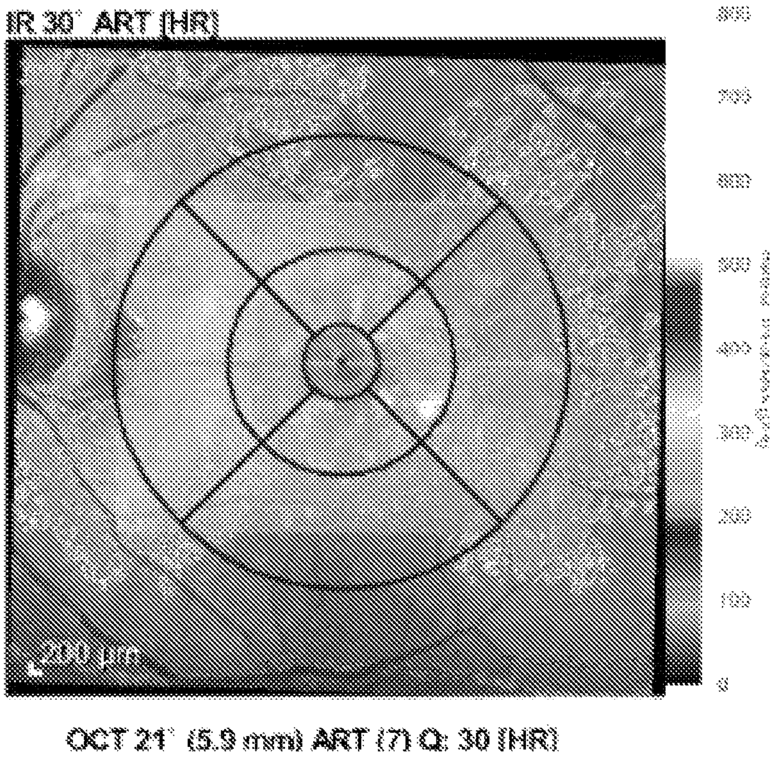
FIG. 3K shows representative fundus photography for patient 2 (OS) (test date 8-5-16).
Figure 3L:
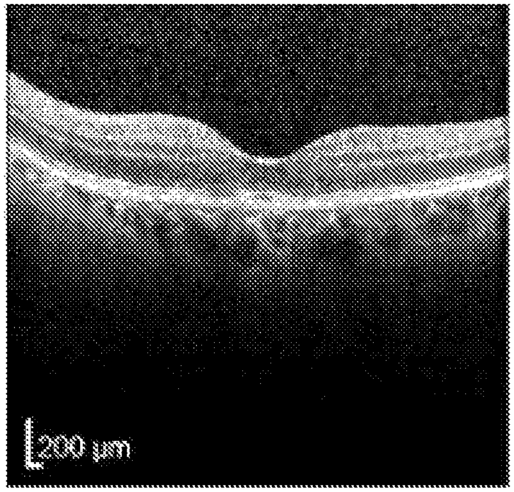
FIG. 3L shows representative OCT retinal imaging for patient 2 (OS) (test date 8-5-16).
Figure 3M:
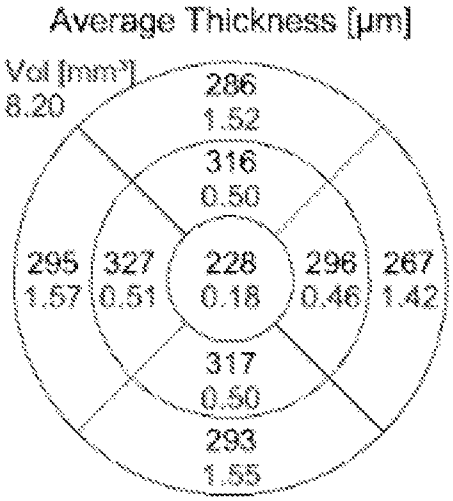
FIG. 3M shows the average thickness (in μM) and average volume ($mm^3$) of the retina as derived from the OCT imaging of FIG. 3L.
Figure 3N:
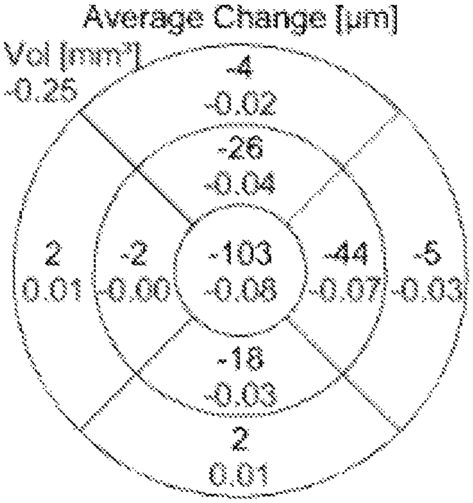
FIG. 3N shows the average change in average thickness (in μM) and average volume ($mm^3$) of the retina as derived from the data in FIGS. 3J and 3M.

Patient 2 underwent OCT retinal imaging for the left eye as described above in February and August 2016. OCT images from the February 2016 test are shown in FIGS. 3H and 3I. FIG. 3J shows average retinal thickness (μM) and average retinal volume ($mm^3$) for the ETDRS segments as determined from analysis of the February 2016 OCT images (using standard software of the OCT imaging system). Average retinal thickness was determined to be 364 μM (minimum of 217 μM and maximum of 457 μM) and average total volume was determined to be 8.45 $mm^3$. OCT images from the August 2016 test are shown in FIGS. 3K and 3L. FIG. 3M shows average retinal thickness (μM) and average retinal volume ($mm^3$) for the ETDRS segments as determined from analysis of the August 2016 OCT images (using standard software of the OCT imaging system). Average retinal thickness was determined to be 193 μM (minimum of 191 μM and maximum of 291 μM) and average total volume was determined to be 8.2 $mm^3$. FIG. 3N shows the average change between February 2016 and August 2016 in retinal thickness and volume over the ETDRS segments. The data show a rapid, substantially complete drusen resolution and an overall decrease in retinal volume of 0.25 $mm^3$.

Figure 4C:
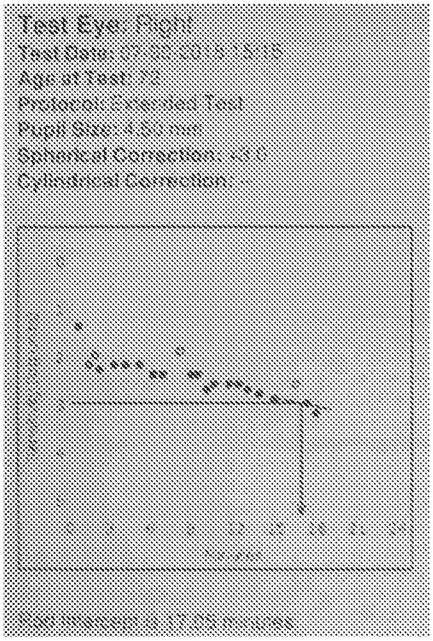
FIG. 4C shows dark adaptation results for patient 2 (OD). The date of the test was 7-30-18 and the patient was 72 years of age on the test date. Pupil size was 4.50 mm. A spherical correction of +3.0 was used. The RI time was determined to be 17.05 min.
Figure 4D:
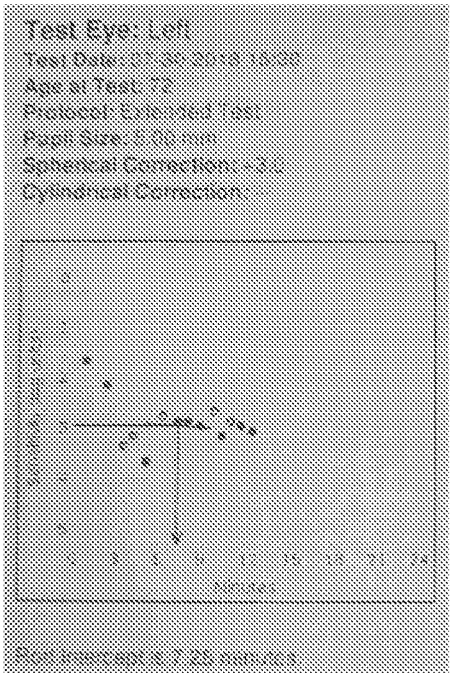
FIG. 4D shows dark adaptation results for patient 2 (OS). The details are the same as in FIG. 4C. The RI time was determined to be 7.28 min.

In May 2018, patient 2 was determined to have visual acuity of 20/30 and 20/20 in the right and left eye respectively (determined as described above). In July 2018, patient 2 underwent additional dark adaptation testing as described above. The results are shown in FIGS. 4C (right eye, OD) and 4D (left eye, OS). The RI times were determined to be 17.05 minutes OD and 7.28 minutes OS, an improvement of 1.67 minutes and 2.60 minutes, respectively, from the previous dark adaptation testing in January 2015.

In patient 2, the dark adaptation RI time parameter showed improvement in both the right eye (OD) and left eye (OS) over the time course of statin therapy. Similarly, clinical assessment showed substantially complete drusen resolution along with a decrease in retinal volume, and the ending diagnosis in July 2018 was determined to have regressed to early AMD in both eyes from the baseline diagnosis of intermediate AMD. The improvement in RI time in both eyes from January 2015 to July 2018 mirrored the observed improvement in retina structure and clinical diagnosis in both eyes over this same time period, and matched the determination of a positive response to statin therapy. Thus, dark adaptation as characterized by the RI time parameter was an accurate biomarker for efficacy of statin therapy in patient 2.

Patient 5

After clinical assessment, patient 5 was diagnosed with intermediate AMD (both eyes, OU). Patient 5 initiated statin therapy with atorvastatin (80 mg per day) in January 2014 and continued statin therapy at this dose until January 2015. After a treatment holiday of thirteen months, statin therapy was resumed in February 2016 with atorvastatin (20 mg/day). In April 2018, the statin therapy was changed to pravastatin (20 mg/day).

Figure 5A:
FIG. 5A shows representative fundus photography and OCT imaging for patient 5 (OD). The date of the test was 1-26-14.
Figure 5B:
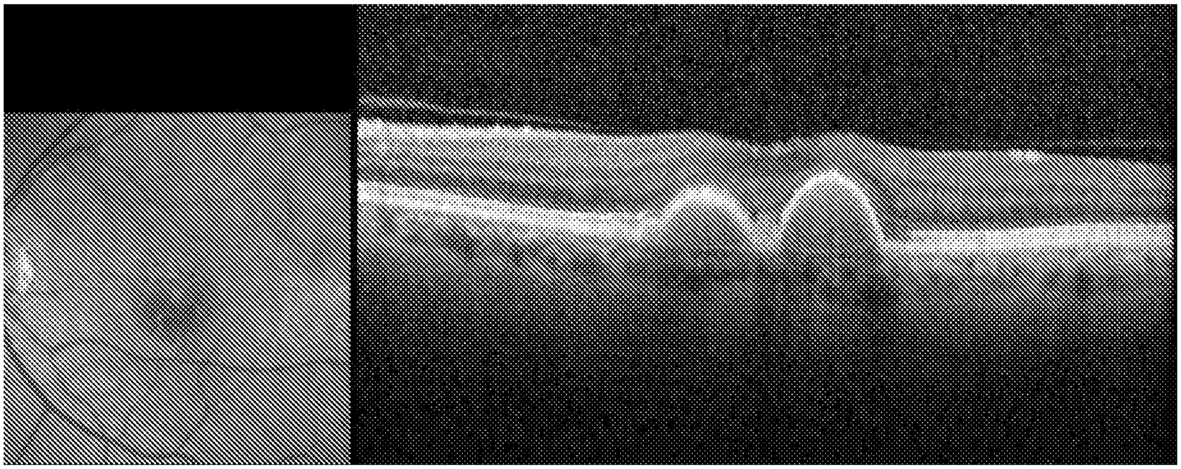
FIG. 5B shows representative fundus photography and OCT imaging for patient 5 (OS). The date of the test was 1-26-14.
Figure 5C:
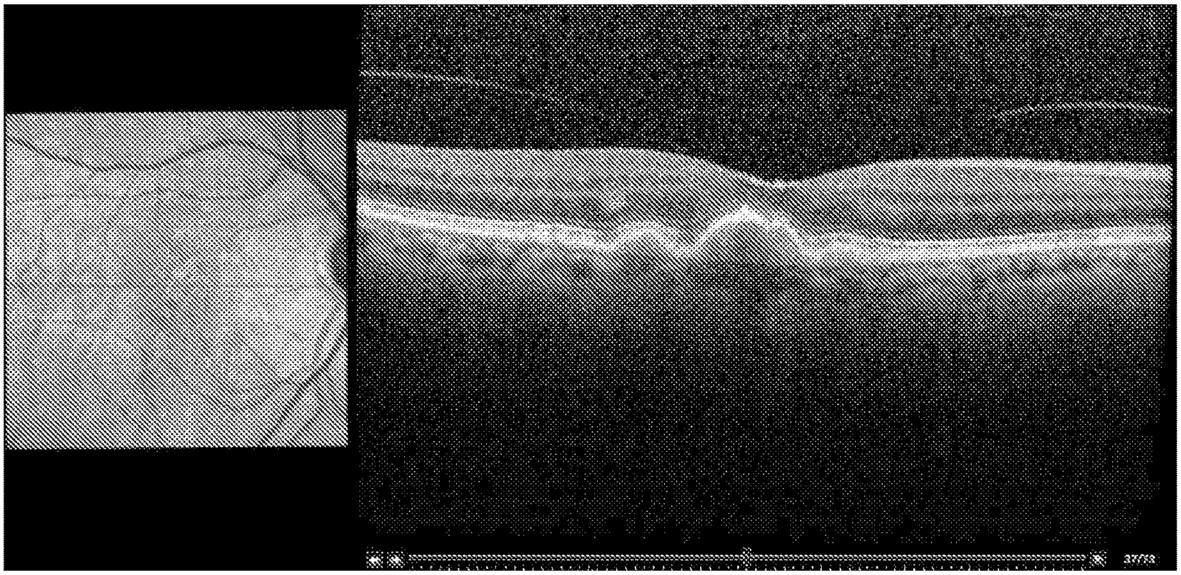
FIG. 5C shows representative fundus photography and OCT imaging for patient 5 (OD). The date of the test was 4-9-18.
Figure 5D:
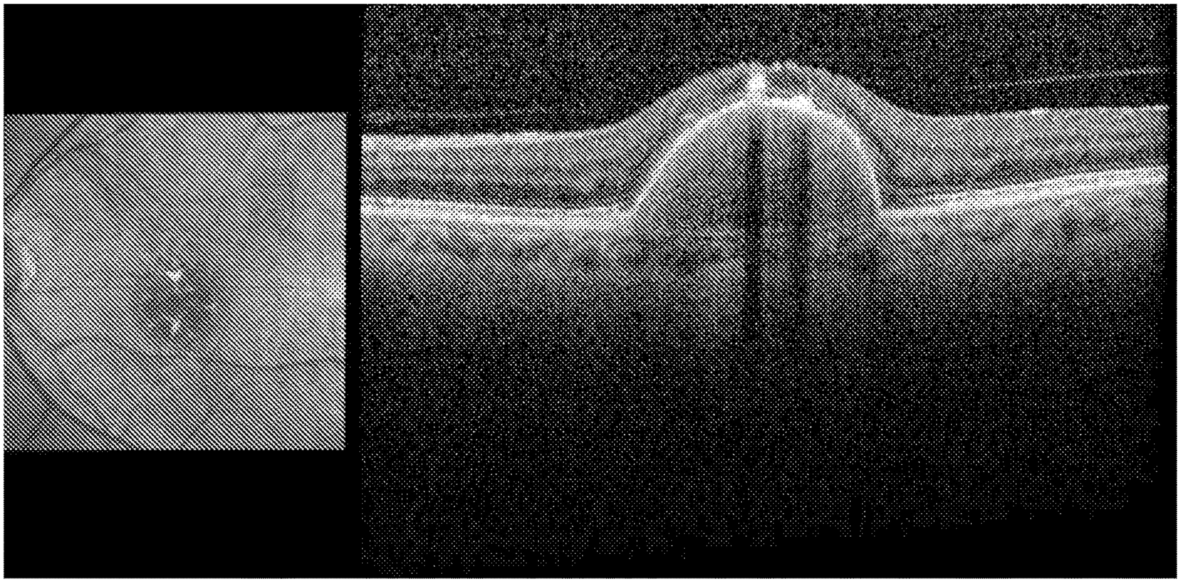
FIG. 5D shows representative fundus photography and OCT imaging for patient 5 (OS). The date of the test was 4-9-18.
Figure 6A:
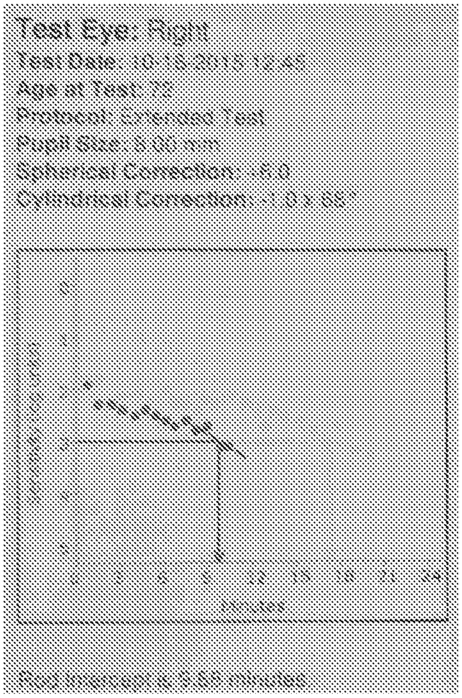
FIG. 6A shows dark adaptation results for patient 5 (OD). The date of the test was 10-16-15 and the patient was 72 years of age on the test date. Pupil size was 8.00 mm. A spherical correction of +6.0 and a cylindrical correction of −1.0×68° was used. The RI time was determined to be 9.68 min.
Figure 6B:
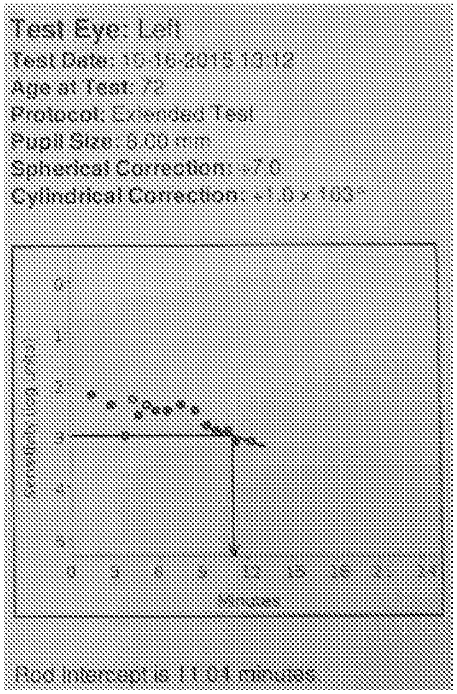
FIG. 6B shows dark adaptation results for patient 5 (OS). The details are the same as in FIG. 6A, with the exception a spherical correction of +7.0 and a cylindrical correction of +1.0×103° was used. The RI time was determined to be 11.04 min.
Figure 6C:
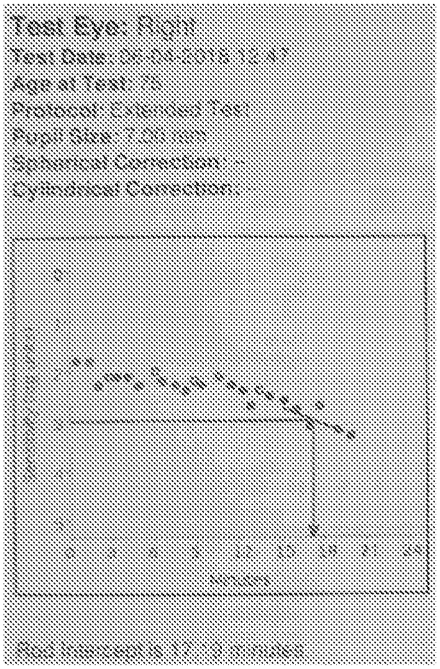
FIG. 6C shows dark adaptation results for patient 5 (OD). The date of the test was 6-4-18 and the patient was 75 years of age on the test date. Pupil size was 7.00 mm. The RI time was determined to be 17.19 min.
Figure 6D:
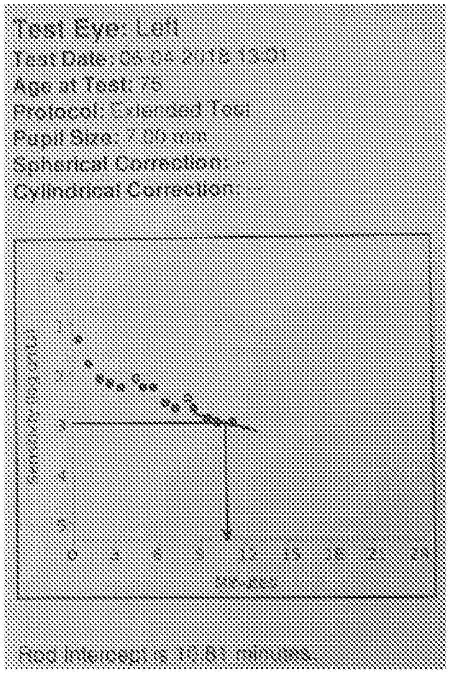
FIG. 6D shows dark adaptation results for patient 5 (OS). The details are the same as in FIG. 6C. The RI time was determined to be 10.81 min.

In January 2014 (concurrent with initiation of statin therapy), patient 5 underwent OCT retinal imaging as described above, the results of which are shown in FIGS. 5A (right eye, OD) and 5B (left eye, OS). As shown in FIGS. 5A and 5B, OCT retinal imaging revealed drusen accumulation in both eyes, consistent with a diagnosis of intermediate AMD. The patient's visual acuity in January 2014 was determined to be 20/25 (both eyes, OU). In October 2015, patient 5 underwent dark adaptation testing as described above to measure RI times for both eyes. The results are shown in FIGS. 6A (right eye, OD) and 6B (left eye, OS). The RI times were determined to be 9.68 minutes (right eye, OD) and 11.04 minutes (left eye, OS). Patient 5 was subsequently examined in April 2018 using OCT retinal imaging and in June 2018 with dark adaptation testing. The results of the April 2018 OCT retinal imaging are shown in FIGS. 5C (right eye, OD) and 5D (left eye, OS) and indicate the continued presence of drusen. More specifically, comparing FIGS. 5A and 5C (right eye at the earlier and later time points, respectively), shows increased drusen accumulation with possible increase in drusen size, and comparing FIGS. 5B and 5D (left eye at the earlier and later time points, respectively) indicates development of a PED at the later time point. The results of the June 2018 dark adaptation testing are shown in FIGS. 6C (right eye, OD) and 6D (left eye, OS) and indicate that RI times were determined to be 17.19 minutes (right eye, OD) and 10.81 minutes (left eye, OS). The RI time for the right eye was increased by 7.51 minutes while the RI time for the left eye remained essentially unchanged from the earlier measurement.

In patient 5, the dark adaptation RI time parameter showed worsening in the right eye (OD) and essentially no change in the left eye (OS) over the time course of statin therapy. Similarly, clinical assessment indicated at least slight disease progression over the course of statin therapy, although patient 5 was still determined to have intermediate AMD. The worsening in RI time in the right eye and the lack of improvement in RI time in the left eye from October 2015 to June 2018 mirrored the observed worsening of retina structure and lack of an improvement in clinical diagnosis in both eyes during this same time period, and matched the determination of no response to statin therapy. Thus, dark adaptation as characterized by the RI time parameter was an accurate biomarker for efficacy of statin therapy in patient 5.

Patient 6

Figure 7A:
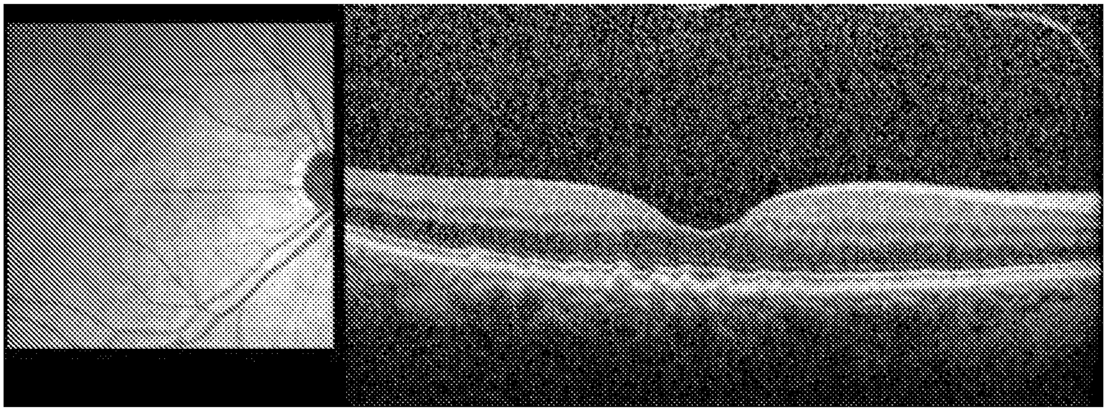
FIG. 7A shows representative fundus photography and OCT imaging for patient 6 (OD) prior to the initiation of high-dose statin therapy.
Figure 7B:
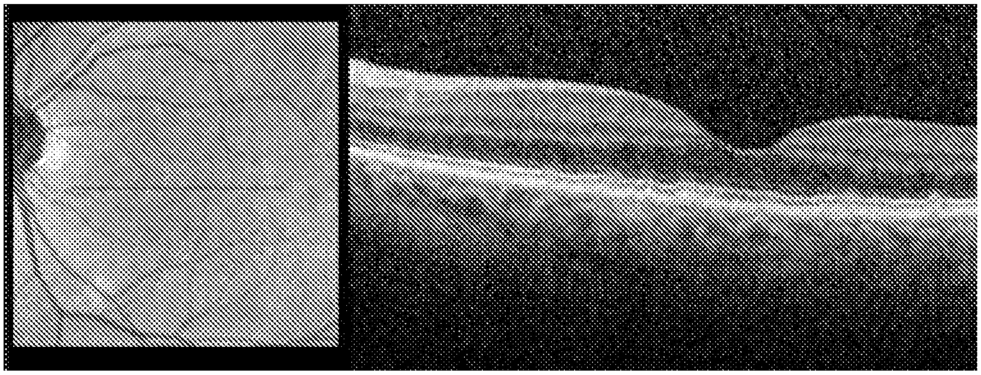
FIG. 7B shows representative fundus photography and OCT imaging for patient 6 (OS) prior to the initiation of high-dose statin therapy.
Figure 8A:
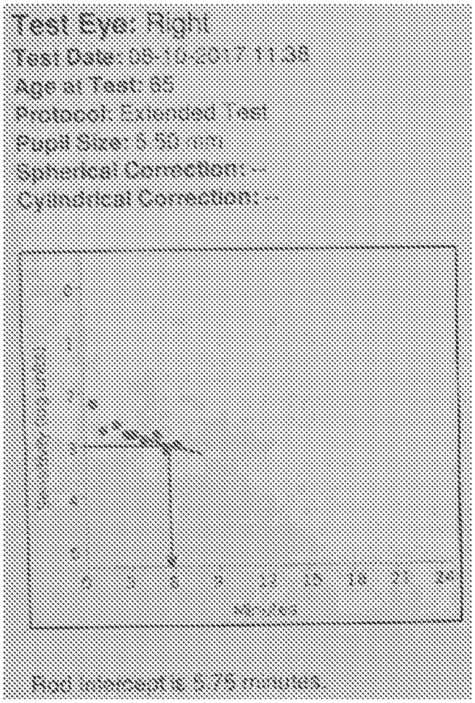
FIG. 8A shows dark adaptation results for patient 6 (OD) shortly before the initiation of high-dose statin therapy. The RI time was determined to be 5.75 min.

After clinical assessment, patient 6 was diagnosed with intermediate AMD (both eyes, OU). As part of the clinical assessment, Patient 6 underwent OCT retinal imaging as described above. The results are shown in FIGS. 7A (right eye, OD) and 7B (left eye, OS). As shown in FIGS. 7A and 7B, OCT retinal imaging revealed mild drusen accumulation in both eyes, consistent with the diagnosis of intermediate AMD. Patient 6 initiated statin treatment with atorvastatin (80 mg per day) in November 2017. In August 2017 (shortly before initiation of statin treatment), patient 6 underwent dark adaptation testing as described above to determine the RI time for the right eye, the results of which are shown in FIG. 8A (right eye, OD). The RI time was determined to be 5.75 minutes. A bleaching error was encountered when testing the left eye of patient 6, preventing determination of the RI time for the left eye.

Figure 7C:
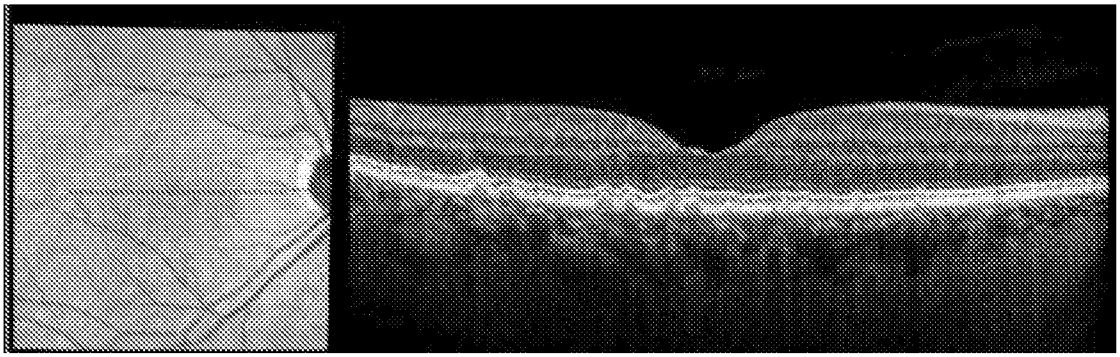
FIG. 7C shows representative fundus photography and OCT imaging for patient 6 (OD) after 9 months of high-dose statin therapy.
Figure 7D:
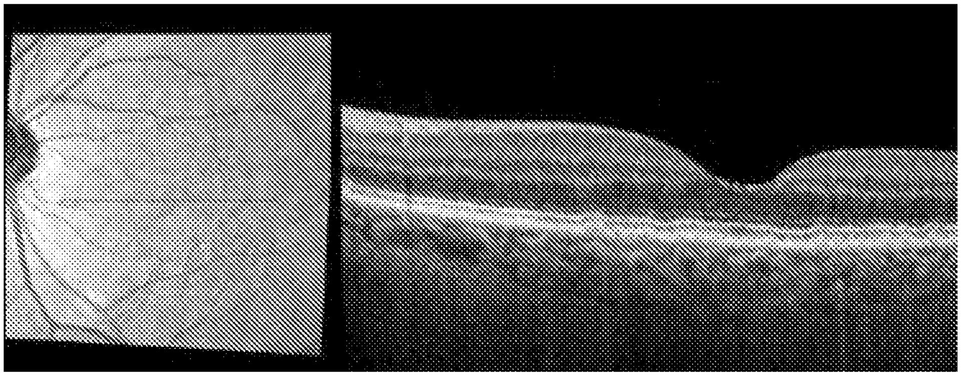
FIG. 7D shows representative fundus photography and OCT imaging for patient 6 (OS) after 9 months of high-dose statin therapy.
Figure 7E:
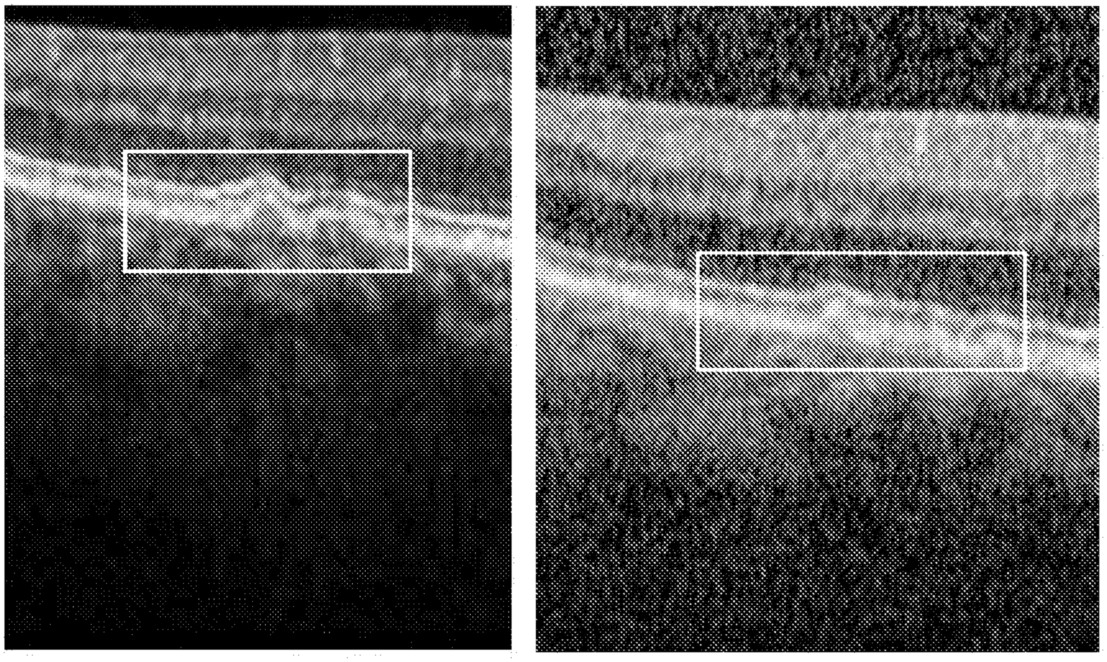
FIG. 7E shows an expanded region from the OCT retinal images of FIGS. 7A and 7C. The left image is prior to the initiation of high-dose statin therapy. The right image is after 9 months of high-dose statin therapy.

Patient 6 continued statin therapy and was subsequently examined in August 2018 using OCT retinal imaging and dark adaptation testing. The results of the August 2018 OCT retinal imaging are shown in FIGS. 7C (right eye, OD) and 7D (left eye, OS). Comparing FIGS. 7A/7B and 7C/7D (earlier/later time points for the right eye and left eye, respectively), hints of drusen resolution can be seen in both eyes. FIG. 7E is an expanded region from the OCT retinal images of FIGS. 7A and 7C (earlier and later time points, respectively, for the right eye) showing slight decreases in drusen size consistent with the initiation of drusen resolution. In addition, analysis of these August 2018 OCT images (using standard software of the OCT imaging system) indicates a decrease in retinal volume of 0.09 $mm^3$ for the right eye (OD) and 0.10 $mm^3$ for the left eye (OS).

Figure 8B:
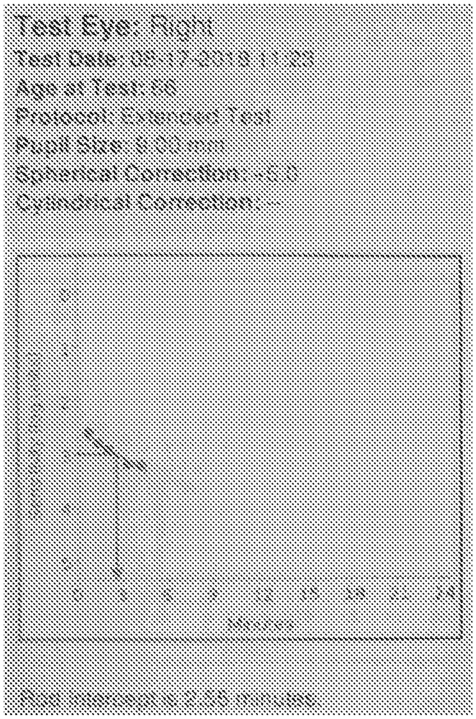
FIG. 8B shows dark adaptation results for patient 6 (OD) after 9 months of high-dose statin therapy. The RI time was determined to be 2.55 min.

The results of the August 2018 dark adaptation testing are shown in FIG. 8B (right eye, OD). The RI time for the right eye was determined to be 2.55 minutes, a decrease of 3.20 minutes from the previous determination in August 2017. A bleaching error again prevented determination of the RI time for the left eye.

In patient 6, the dark adaptation RI time parameter showed improvement in the right eye (OD) by 3.2 minutes over the time course of statin therapy. Similarly, clinical assessment provided signs of a positive clinical response, although patient 6 was still classified as intermediate AMD. Hints of a positive clinical response reinforced by improvement in dark adaptation function after a relatively brief (nine month) course of treatment indicate that statin therapy should be continued for patient 6. Thus, dark adaptation as characterized by the RI time parameter was a useful biomarker for potential success of statin therapy in patient 6.

Patient 7

Figure 9A:
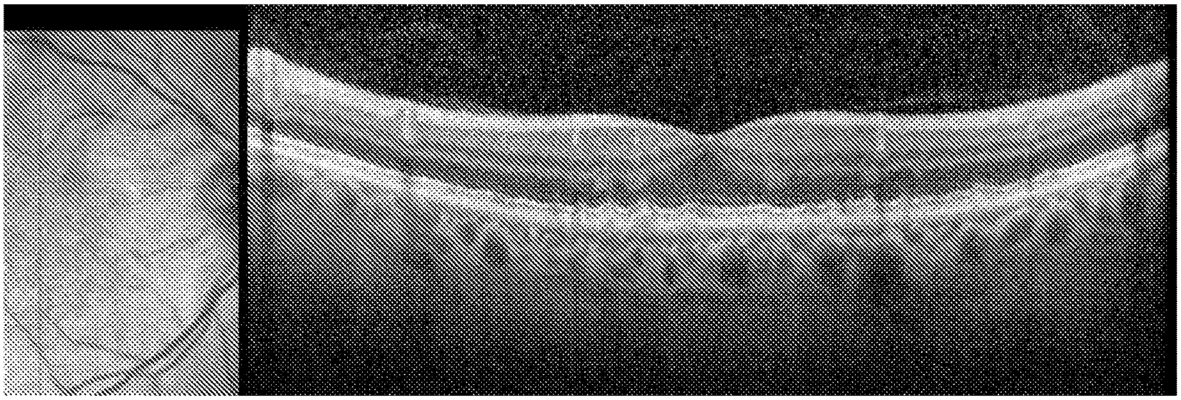
FIG. 9A shows representative fundus photography and OCT imaging for patient 7 (OD) prior to the initiation of low-dose statin therapy.
Figure 9B:
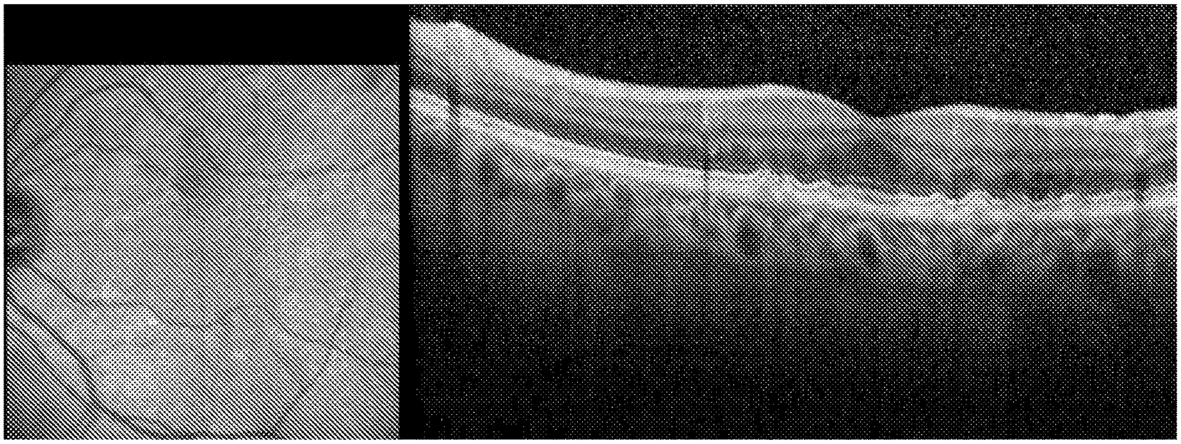
FIG. 9B shows representative fundus photography and OCT imaging for patient 7 (OS) prior to the initiation of low-dose statin therapy.
Figure 9C:
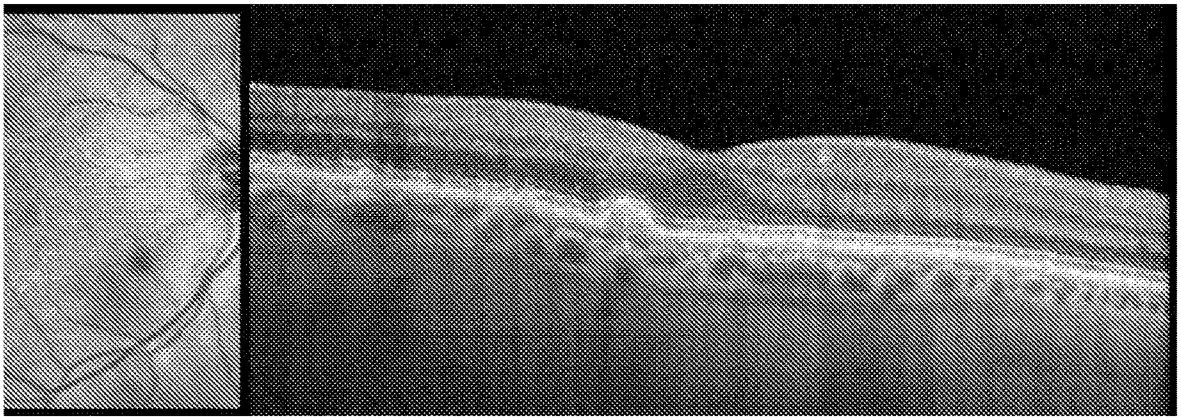
FIG. 9C shows representative fundus photography and OCT imaging for patient 7 (OD) after 27 months of low-dose statin therapy.
Figure 9D:
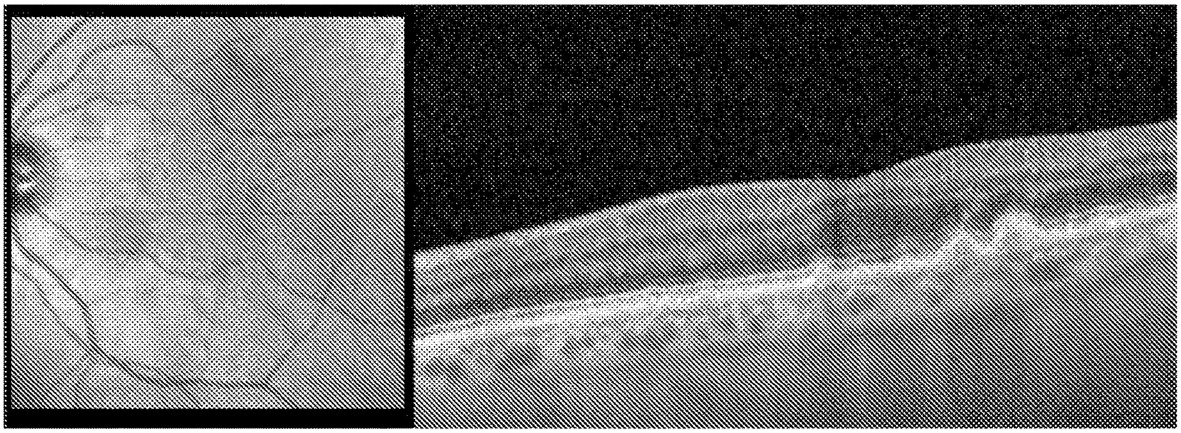
FIG. 9D shows representative fundus photography and OCT imaging for patient 7 (OS) after 27 months of low-dose statin therapy.
Figure 10A:
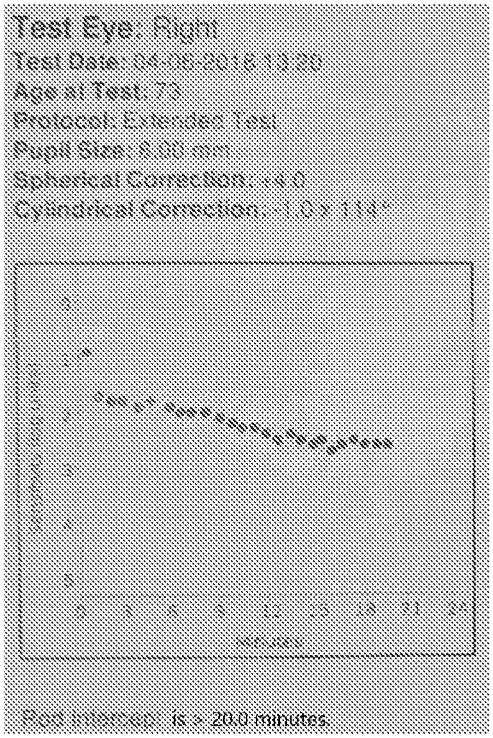
FIG. 10A shows dark adaptation results for patient 7 (OD) prior to the initiation of low-dose statin therapy. The RI time was determined to be over 20 min.
Figure 10B:
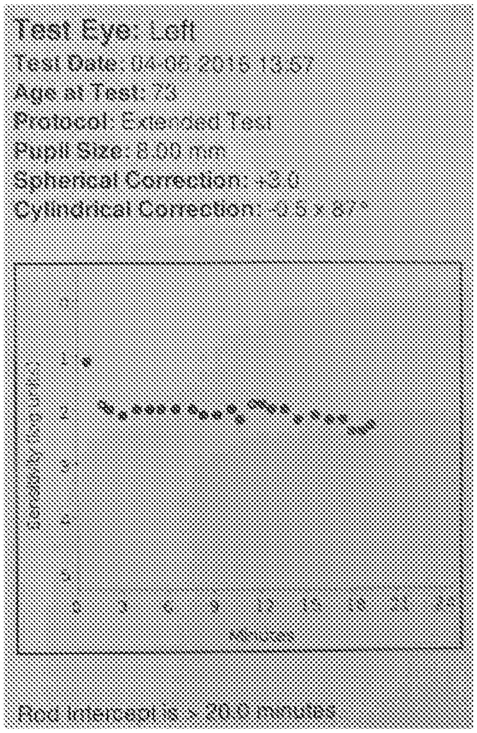
FIG. 10B shows dark adaptation results for patient 7 (OS) prior to the initiation of low-dose statin therapy. The RI time was determined to be over 20 min.
Figure 10C:
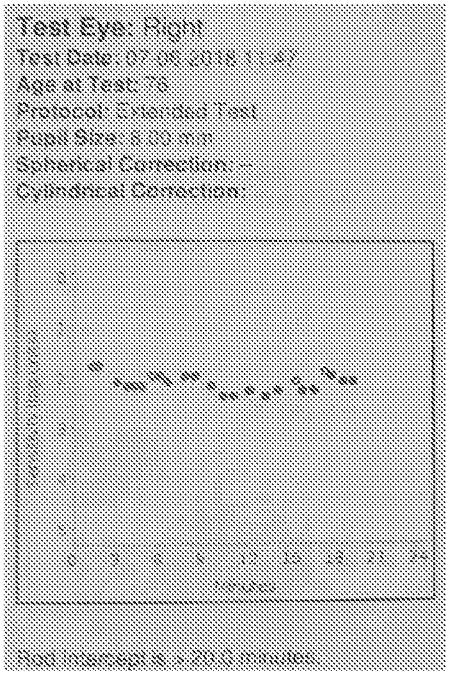
FIG. 10C shows dark adaptation results for patient 7 (OD) after 27 months of low-dose statin therapy. The RI time was determined to be over 20 min.
Figure 10D:
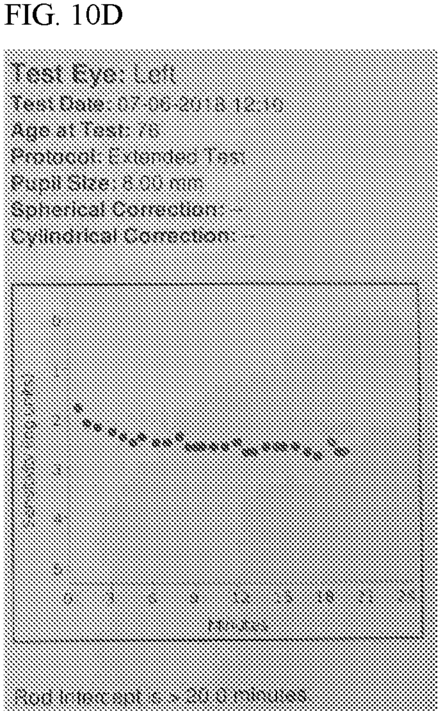
FIG. 10D shows dark adaptation results for patient 7 (OS) after 27 months of low-dose statin therapy. The RI time was determined to be over 20 min.

After clinical assessment, patient 7 was diagnosed with intermediate AMD (both eyes, OU). Patient 7 initiated statin treatment with atorvastatin (10-20 mg per day) in April 2016. In March 2016 (prior to initiation of statin therapy), patient 7 underwent OCT retinal imaging as described above, the results of which are shown in FIGS. 9A (right eye, OD) and 9B (left eye, OS). As shown in FIGS. 9A and 9B, OCT retinal imaging revealed drusen accumulation in both eyes, consistent with a diagnosis of intermediate AMD. At the initiation of statin treatment in April 2016, patient 7 underwent dark adaptation testing as described above to measure RI times in both eyes, the results of which are shown in FIGS. 10A (right eye, OD) and 10B (left eye, OS). The RI times were determined to be over 20 minutes in both eyes. Patient 7 continued statin therapy and was subsequently examined in July 2018 using OCT retinal imaging and dark adaptation testing. The results of the July 2018 OCT retinal imaging are shown in FIGS. 9C (right eye, OD) and 9D (left eye, OS), and again show the presence of drusen with no apparent reduction in both eyes. The results of July 2018 dark adaptation testing are shown in FIGS. 10C (right eye, OD) and 10D (left eye, OS), and again show RI times over 20 minutes in both eyes (unchanged from the initial dark adaptation testing at the initiation of statin therapy).

In patient 7, the dark adaptation RI time parameter showed no improvement over the time course of statin therapy. Similarly, clinical assessment indicates that the disease remained stable with no signs of improvement over the course of statin therapy. The statin dose administered to patient 7 was very low (10-20 mg/day). Current research indicates that higher statin doses (for example, 40-80 mg/day) may be more effective in treating AMD, particularly early and intermediate AMD. Absence of a positive clinical response reinforced by no improvement in dark adaptation function after a relatively long (27 month) course of treatment indicate that statin therapy should be discontinued for patient 7 or modified to administer a higher dose. Thus, dark adaptation as characterized by the RI time parameter was a useful biomarker for likely failure of statin therapy in patient 7.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining the effectiveness of treating a subject having age-related macular degeneration (AMD) in a clinical trial of a statin therapy for AMD, the method consisting of the steps of:

a. measuring one or more functional biomarkers in the subject having AMD, wherein the functional biomarker is a visual function other than normal luminance visual acuity;

b. determining a baseline value for the subject from the one or more measurements of step a;

c. administering the statin therapy to the subject having AMD after step a;

d. measuring the one or more functional biomarkers in the subject at one or more later time points after step c;

e. determining a corresponding subsequent value for the subject from the one or more measurements of step d;

f. using a comparison of the subsequent value to the baseline value or an earlier subsequent value as a clinical trial endpoint to determine the effectiveness of the treatment; and g. taking an action based on the clinical trial endpoint.

2. The method of claim 1, wherein measuring the one or more functional biomarkers comprises measuring one or more of dark adaptation, low luminance visual acuity, low luminance deficit, contrast sensitivity, or scotopic sensitivity.

3. The method of claim 1, wherein the functional biomarker is dark adaptation.

4. The method of claim 3, wherein the baseline value and subsequent value are a rod intercept time.

5. The method of claim 4, wherein the rod intercept time is determined using a dark adaptometer under the following conditions:

a. a 70% effective bleach and a 5° or 12° eccentricity test location;

b. a 76% effective bleach and a 5° or 12° eccentricity test location;

c. a 70% effective bleach and a 5° eccentricity test location;

d. a 70% effective bleach and a 12° eccentricity test location;

e. a 76% effective bleach and a 5° eccentricity test location; or f. a 76% effective bleach and a 12° eccentricity test location.

6. The method of claim 5, wherein the 5° or 12° eccentricity test location are centered on the inferior visual meridian.

7. The method of claim 5, wherein a rod intercept criterion sensitivity level is from $5\times10^{-2}$ scotopic cd/m$^2$ to $5\times10^{-4}$ scotopic cd/m$^2$ or is $5\times10^{-3}$ scotopic cd/m$^2$.

8. The method of claim 1, wherein the statin therapy is atorvastatin at a dose from 40 mg to 120 mg daily.

9. The method of claim 1, wherein the statin therapy is cerivastatin, fluvastatin, lovastatin, pitavastatin, rosuvastatin, or simvastatin at a dose from 40 mg dose equivalent to atorvastatin to 120 mg dose equivalent to atorvastatin daily.

10. The method of claim 1, wherein the clinical trial endpoint is a primary or registration endpoint or a secondary or exploratory endpoint.

11. The method of claim 1, wherein the action based on the clinical trial endpoint is to determine efficacy at the conclusion of the clinical trial or to provide an early indication of efficacy at an interim period during the clinical trial.

12. The method of claim 11, wherein the early indication of efficacy is established if the comparison of the subsequent value to the baseline value or an earlier subsequent value satisfies an early indication criteria.

13. The method of claim 12, wherein the early indication criteria is:

a. no change in the subsequent value as compared to the baseline value or an earlier subsequent value;

b. an improvement in the subsequent value as compared to the baseline value or an earlier subsequent value; or c. a worsening of less than 10% in the subsequent value as compared to the baseline value or an earlier subsequent value.

14. The method of claim 12, wherein the baseline value, the subsequent value and the earlier subsequent value are each a rod intercept time.

15. The method of claim 14, wherein the early indication criteria is:

a. no change in the subsequent value as compared to the baseline value or an earlier subsequent value;
b. an improvement in the subsequent value as compared to the baseline value or an earlier subsequent value; or
c. a worsening of less than 180 seconds in the subsequent value as compared to the baseline value or an earlier subsequent value.

16. The method of claim 1, wherein the action is a. making a decision on continuing the clinical trial;
b. terminating the clinical trial;
c. adding additional subjects to the clinical trial;
d. changing a parameter of the clinical trial; or
e. a combination of the foregoing.

17. The method of claim 1, the method consisting of the steps of:

a. measuring a functional biomarker in the subject having AMD, wherein the functional biomarker is a visual function other than normal luminance visual acuity;
b. determining a baseline value for the subject from the measurement of step a;
c. administering the statin therapy to the subject having AMD after step a;
d. measuring the functional biomarker in the subject at one or more later time points after step c;
e. determining a corresponding subsequent value for the subject from the one or more measurements of step d;
f. using a comparison of the subsequent value to the baseline value or an earlier subsequent value as a clinical trial endpoint to determine the effectiveness of the treatment; and
g. taking an action based on the clinical trial endpoint.

18. A method for stratifying a plurality of subjects who have age-related macular degeneration (AMD) and are participating in a clinical trial of a statin therapy for treatment of AMD, the method consisting of the steps of:

a. measuring one or more functional biomarkers in each of the plurality of subjects, wherein the functional biomarker is a visual function other than normal luminance visual acuity;
b. determining a subject value for each of the plurality of subjects from the one or more measurements of step a to provide a subject value for each of the plurality subjects;
c. stratifying the plurality of subjects based on the subject values; and
d. administering the statin therapy to the plurality of subjects stratified in step c.

19. The method of claim 18, wherein measuring the one or more functional biomarkers comprises measuring one or more of dark adaptation, low luminance visual acuity, low luminance deficit, contrast sensitivity, or scotopic sensitivity.

20. The method of claim 18, the method consisting of the steps of:

a. measuring a functional biomarker in each of the plurality of subjects, wherein the functional biomarker is a visual function other than normal luminance visual acuity;
b. determining a subject value for each of the plurality of subjects from the measurement of step a to provide a subject value for each of the plurality subjects;
c. stratifying the plurality of subjects based on the subject values; and
d. administering the statin therapy to the plurality of subjects stratified in step c.

21. A method for identifying an early indication of a response to treating a subject having age-related macular degeneration (AMD) in a clinical trial of a statin therapy for AMD, the method consisting of the steps of:

a. measuring one or more functional biomarkers in the subject having AMD, wherein the functional biomarker is a visual function other than normal luminance visual acuity;
b. determining a baseline value for the subject from the one or more measurements of step a;
c. administering the statin therapy to the subject having AMD after step a;
d. measuring the one or more functional biomarkers in the subject at one or more later time points after step c;
e. determining a corresponding subsequent value from the one or more measurements of step d; and
f. identifying the early indication of a response to the statin therapy in the subject if a comparison of the subsequent value to the baseline value or an earlier subsequent value satisfies an early indication criteria.

22. The method of claim 21, wherein measuring the one or more functional biomarkers comprises measuring one or more of dark adaptation, low luminance visual acuity, low luminance deficit, contrast sensitivity, or scotopic sensitivity.

23. The method of claim 21, the method consisting of the steps of:

a. measuring a functional biomarker in the subject having AMD, wherein the functional biomarker is a visual function other than normal luminance visual acuity;
b. determining a baseline value for the subject from the measurement of step a;
c. administering the statin therapy to the subject having AMD after step a;
d. measuring the functional biomarker in the subject at one or more later time points after step c;
e. determining a corresponding subsequent value from the one or more measurements of step d; and
f. identifying the early indication of a response to the statin therapy in the subject if a comparison of the subsequent value to the baseline value or an earlier subsequent value satisfies an early indication criteria.

24. A method for selecting or identifying a subject having age-related macular degeneration (AMD) for participation in a clinical trial of a statin therapy for AMD, the method consisting of the steps of:

a. measuring one or more functional biomarkers in the subject, wherein the functional biomarker is a visual function other than normal luminance visual acuity;
b. determining a subject value for the subject from the one or more measurements of step a;
c. comparing the subject value to a corresponding reference range;
d. selecting or identifying the subject for participation if the subject value is within the corresponding reference range; and
e. administering the statin therapy to the subject selected or identified for participation in step d.

25. The method of claim 24, wherein measuring the one or more functional biomarkers comprises measuring one or more of dark adaptation, low luminance visual acuity, low luminance deficit, contrast sensitivity, or scotopic sensitivity.

26. The method of claim 24, the method consisting of the steps of:
a. measuring a functional biomarker in the subject, wherein the functional biomarker is a visual function other than normal luminance visual acuity;
b. determining a subject value for the subject from the measurement of step a;
c. comparing the subject value to a corresponding reference range;
d. selecting or identifying the subject for participation if the subject value is within the corresponding reference range; and
e. administering the statin therapy to the subject selected or identified for participation in step d.

27. A method for treating a subject suffering from age-related macular degeneration (AMD) with a statin, the method consisting of the steps of:
a. measuring one or more functional biomarkers in the subject;
b. determining a baseline value for the subject from the one or more measurements of step a;
c. administering a statin treatment to the subject at an initial statin dose;
d. measuring the one or more functional biomarkers in the subject at one or more later time points, wherein the functional biomarker is a visual function other than normal luminance visual acuity;
e. determining a subsequent value for the subject from the one or more measurements of step d; and
f. making a treatment decision based on the subsequent value and the baseline value or the subsequent value and an earlier subsequent value, wherein the treatment decision is:
i. continuing administering the statin treatment without change;
ii. continuing administering the statin treatment with an increase in the dose of the statin being administered as compared to the initial dose or decrease in the dose of the statin being administered as compared to the initial dose;
iii. continuing administering statin treatment with a different statin either at the same equivalent dose as compared to the initial dose, a higher equivalent dose as compared to the initial dose, or a lower equivalent dose as compared to the initial dose; or
iv. discontinuing the statin treatment.

28. The method of claim 27, wherein measuring the one or more functional biomarkers comprises measuring one or more of dark adaptation, low luminance visual acuity, low luminance deficit, contrast sensitivity, or scotopic sensitivity.

29. The method of claim 27, the method consisting of the steps of:
a. measuring a functional biomarker in the subject;
b. determining a baseline value for the subject from the measurement of step a;
c. administering a statin treatment to the subject at an initial statin dose;
d. measuring the functional biomarker in the subject at one or more later time points, wherein the functional biomarker is a visual function other than normal luminance visual acuity;
e. determining a subsequent value for the subject from the one or more measurements of step d; and
f. making a treatment decision based on the subsequent value and the baseline value or the subsequent value and an earlier subsequent value, wherein the treatment decision is:
i. continuing administering the statin treatment without change;
ii. continuing administering the statin treatment with an increase in the dose of the statin being administered as compared to the initial dose or decrease in the dose of the statin being administered as compared to the initial dose;
iii. continuing administering statin treatment with a different statin either at the same equivalent dose as compared to the initial dose, a higher equivalent dose as compared to the initial dose, or a lower equivalent dose as compared to the initial dose; or
iv. discontinuing the statin treatment.

30. A method of selecting and treating a subject suffering from age-related macular degeneration (AMD), the method consisting of the steps of:
a. measuring one or more functional biomarkers in the subject, wherein the functional biomarker is a visual function other than normal luminance visual acuity;
b. determining a subject value for the subject from the one or more measurements of step a;
c. comparing the subject value to a corresponding reference range;
d. selecting the subject for treatment with the statin therapy if the subject value falls within the reference range or not selecting the subject for treatment with the statin therapy if the subject value falls outside the reference range; and
e. administering the statin therapy to the subject selected for treatment in step d, thereby treating said AMD in said subject.

31. The method of claim 30, wherein measuring the one or more functional biomarkers comprises measuring one or more of dark adaptation, low luminance visual acuity, low luminance deficit, contrast sensitivity, or scotopic sensitivity.

32. The method of claim 30, the method consisting of the steps of:
a. measuring a functional biomarker in the subject, wherein the functional biomarker is a visual function other than normal luminance visual acuity;
b. determining a subject value for the subject from the measurement of step a;
c. comparing the subject value to a corresponding reference range;
d. selecting the subject for treatment with the statin therapy if the subject value falls within the reference range or not selecting the subject for treatment with the statin therapy if the subject value falls outside the reference range; and
e. administering the statin therapy to the subject selected for treatment in step d, thereby treating said AMD in said subject.

33. A method for treating a subject suffering from age-related macular degeneration (AMD) with a statin, the method consisting of the steps of:
a. measuring one or more functional biomarkers in the subject;
b. determining a baseline value for the subject from the one or more measurements of step a;
c. administering a statin treatment to the subject at an initial statin dose;

d. measuring the one or more functional biomarkers in the subject at one or more later time points, wherein the functional biomarker is a visual function other than normal luminance visual acuity;

e. determining a subsequent value for the subject from the one or more measurements of step d; and f. administering a statin treatment to the subject based on the subsequent value and the baseline value or the subsequent value and an earlier subsequent value, thereby treating said AMD in said subject.

34. The method of claim 33, wherein the statin treatment of step f is i. without change to the dose as compared to the initial dose;

ii. an increase in the dose of the statin being administered as compared to the initial dose or a decrease in the dose of the statin being administered as compared to the initial dose; or iii. with a different statin either at the same equivalent dose as compared to the initial dose, a higher equivalent dose as compared to the initial dose, or a lower equivalent dose as compared to the initial dose.

35. The method of claim 33, wherein measuring the one or more functional biomarkers comprises measuring one or more of dark adaptation, low luminance visual acuity, low luminance deficit, contrast sensitivity, or scotopic sensitivity.

36. The method of claim 33, said method consisting of the steps of:

a. measuring a functional biomarker in the subject;

b. determining a baseline value for the subject from the measurements of step a;

c. administering a statin treatment to the subject at an initial statin dose;

d. measuring the functional biomarker in the subject at one or more later time points, wherein the functional biomarker is a visual function other than normal luminance visual acuity;

e. determining a subsequent value for the subject from the one or more measurements of step d; and f. administering a statin treatment to the subject based on the subsequent value and the baseline value or the subsequent value and an earlier subsequent value, thereby treating said AMD in said subject.

* * * * *